(12) United States Patent
Elmér

(10) Patent No.: US 9,040,487 B2
(45) Date of Patent: May 26, 2015

(54) CYCLOSPORINE EMULSION

(75) Inventor: Eskil Elmér, Lund (SE)

(73) Assignee: NEUROVIVE PHARMACEUTICAL AB, Lund (SE)

( * ) Notice: Subject to any disclaimer, the term of this patent is extended or adjusted under 35 U.S.C. 154(b) by 0 days.

(21) Appl. No.: 13/877,326

(22) PCT Filed: Sep. 30, 2011

(86) PCT No.: PCT/EP2011/067117
§ 371 (c)(1),
(2), (4) Date: Aug. 23, 2013

(87) PCT Pub. No.: WO2012/042023
PCT Pub. Date: Apr. 5, 2012

(65) Prior Publication Data
US 2013/0323270 A1 Dec. 5, 2013

Related U.S. Application Data

(60) Provisional application No. 61/388,633, filed on Oct. 1, 2010.

(30) Foreign Application Priority Data

Oct. 1, 2010 (DK) .................................. 2010 00891

(51) Int. Cl.
*A61K 38/13* (2006.01)
*A61K 47/44* (2006.01)
*C07K 7/64* (2006.01)
*A61K 9/107* (2006.01)
*A61K 47/10* (2006.01)
*A61K 47/12* (2006.01)
*A61K 47/14* (2006.01)
*A61K 47/24* (2006.01)

(52) U.S. Cl.
CPC .................. *A61K 47/44* (2013.01); *A61K 9/107* (2013.01); *A61K 38/13* (2013.01); *A61K 47/10* (2013.01); *A61K 47/12* (2013.01); *A61K 47/14* (2013.01); *A61K 47/24* (2013.01)

(58) Field of Classification Search
None
See application file for complete search history.

(56) References Cited

FOREIGN PATENT DOCUMENTS

| EP | 0361928 | A2 | 4/1990 |
| EP | 0570829 | A1 | 11/1993 |
| EP | 0799620 | A1 | 10/1997 |
| EP | 1929996 | A2 | 6/2008 |
| WO | 97/36610 | A1 | 10/1997 |
| WO | 01/45673 | A1 | 6/2001 |

OTHER PUBLICATIONS

Machine translation of EP 0570829 A1, pp. 1-24, accessed Sep. 18, 2013.*
Izutsu, Therapeutic proteins, methods and protocols, Humana press, edited by C. Mark Smales and David C. James, 2005, pp. 287-292.*
Machine translation of WO 01/45673 A1, published Jun. 28, 2001, enclosed p. 1-14.*
Definition of cyclosporine, from http://medical-dictionary.thefreedictionary.com/p/cyclosporine, pp. 1-5, accessed Mar. 27, 2014.*
Egg lecithin, from http://www.livestrong.com/article/459593-amount-of-lecithin-in-eggs/, pp. 1-9, accessed Apr. 24, 2014.*
Glycerol, from http://www.naturalwellbeing.com/learning-center/Glycerol, pp. 1-3, accessed Apr. 24, 2014.*
Water, from http://www.biology-online.org/dictionary/Water, pp. 1-3, accessed Apr. 24, 2014.*
Coconut oil, from http://www.gnc.com/GNC-SuperFoods-Coconut-Oil/product.jsp?productId=17440856, pp. 1-2, accessed Apr. 24, 2014.*
Lipid Metabolism, from http://oregonstate.edu/dept/biochem/hhmi/hhmiclasses/biochem/lectnoteskga/lecturenotes0 . . . , pp. 1- 5, accessed Apr. 24, 2014.*
Definition of medium-chain triglyceride-1, from http://medical-dictionary.thefreedictionary.com/p/medium-chain%20triglycerides, p. 1, accessed Aug. 27, 2014.*
Definition of medium-chain triglycerides-2, from http://medical-dictionary.thefreedictionary.com/p/medium-chain%20triglycerides%20(MCT), p. 1, accessed Aug. 27, 2014.*
International Preliminary Report on Patentability received for PCT Patent Application No. PCT/EP2011/067117 mailed on Dec. 21, 2012, 9 pages.
International Search Report received for PCT Patent Application No. PCT/EP2011/067117 mailed on Apr. 12, 2012, 4 pages.

* cited by examiner

*Primary Examiner* — Julie Ha
*Assistant Examiner* — Li Ni Komatsu
(74) *Attorney, Agent, or Firm* — Foley & Lardner LLP

(57) ABSTRACT

The present invention relates to a cyclosporine emulsion containing: i) a cyclosporine ii) a natural oil (long chain triglyceride) iii) a phosphatidylcholine, iv) glycerol, v) a pharmaceutically tolerable alkali salt of a free fatty acid, vi) a medium chain triglyceride-oil vii) optionally, hydrochloric acid or sodium hydroxide for pH adjustment viii) water.

4 Claims, 6 Drawing Sheets

Structural formula:

CYCLOSPORINE EMULSION

CROSS-REFERENCE TO RELATED PATENT APPLICATIONS

This application is the U.S. national stage of PCT/EP2011/067117, filed Sep. 30, 2011, and claims priority to U.S. Provisional Application 61/388,633, filed Oct. 1, 2010, and Denmark Application PA 2010 00891, filed Oct. 1, 2010.

BACKGROUND OF THE INVENTION

1. Field of the Invention

The present invention relates to a novel cyclosporine composition in the form of an emulsion with a content of medium chain triglycerides. The emulsion is an oil-in-water emulsion, is bioequivalent to the marketed product SANDIMMUNE® but has an improved tolerability profile compared with SANDIMMUNE®.

2. Background of the Invention

Cyclosporine is a widely used immunosuppressant in organ and tissue transplantation. Cyclosporine has poor solubility in water, and a marketed product SANDIMMUNE® for infusion has been formulated as a concentrate containing 50 mg/ml cyclosporine and polyoxylated castor oil (CREMOPHOR EL®) in ethanol and must be diluted with an isotonic solution of sodium chloride or a 5% solution of glucose before administration. However, intravenous administration of cyclosporine composition containing CREMOPHOR EL® has been associated with hypersensitivity reactions, with responses ranging from mild skin reactions to anaphylaxis and cardiac collapse. Thus, there is a need for CREMOPHOR®-free cyclosporine compositions as well as ready-to-use compositions.

CREMOPHOR EL® is the registered trademark of BASF Corp. for its version of polyethoxylated castor oil. It is prepared by reacting 35 moles of ethylene oxide with each mole of castor oil. The resulting product is a mixture (CAS number 61791-12-6): the major 4846-7352-0668.1 component is the material in which the hydroxyl groups of the castor oil triglyceride have ethoxylated with ethylene oxide to form polyethylene glycol ethers. Minor components are the polyethylene glycol esters of ricinoleic acid, polyethylene glycols and polyethylene glycol ethers of glycerol. Cremophor EL is a synthetic, nonionic surfactant. Its utility comes from its ability to stabilize emulsions of nonpolar materials in aqueous systems.

A number of Cremophor products are available from BASF (Cremophor RH 40 (polyoxyl-40 hydrogenated castor oil), Cremophor EL (polyoxyl-35 castor oil), Cremophor ELP (extra pure grade of EL), which all are grades of polyoxyl castor oil, and Cremophor A 6 (macrogol-6-cetostearyl ether) and Cremophor A 25 (macrogol-25-cetostearyl ether), which are grades of macrogol cetostearyl ethers. To the best of our knowledge, at present only CREMOPHOR EL® has been associated with hypersensitivity reactions. However, it is likely that all the CREMOPHOR® products from the polyoxyl castor oil series have the same side-effect when administered to a subject.

SUMMARY OF THE INVENTION

Ready-to-use compositions of cyclosporine for parenteral administration have been described in inter alia EP-B-0 570 829. However, further developments of such compositions have been necessary in order to obtain compositions that are bioequivalent to the SANDIMMUNE® product and in order to ensure a proper shelf-life.

Further developments are directed at ensuring formulations which can both have sufficient stability and shelf-life as to fulfill the requirements for marketing and distribution in commercial pharmaceuticals business while being bioequivalent and using ingredients which are beneficial to therapeutic targets such as mitochondrial metabolism and being non-toxic.

In clinical practice, this also means that we can better achieve the goal of e.g. SANDIMMUNE® and thereby ensure that in clinical practice it is possible to avoid the adverse effect of CREMOPHOR® and ethanol and avoid having to premedicate with corticosteroids and/or antihistamines in cases where such pretreatment or multi-pharmacy approach is contraindicated.

The present invention provides a Cremophor-free cyclosporine composition for parenteral administration, notably intravenous administration.

A composition of the present invention contains:
A cyclosporine
A natural oil (long chain triglyceride) (e.g. soy-bean oil)
A phosphatidylcholine (e.g. egg lecithin)
Glycerol
A pharmaceutically tolerable alkali salt of a free fatty acid (e.g. sodium oleate)
Medium chain triglyceride-oil (e.g. coconut and/or palm oil)
Optionally, hydrochloric acid or sodium hydroxide for pH adjustment
Water.

A composition of the present invention has an osmolality in the isoosmolar range, i.e. the osmolarity is in a range of from about 280 mosm/l to about 305 mosm/l, preferably about 295-300 mosm/l, which correspond to the value of plasma, i.e. the isoosmolar value. The use of a cyclosporine-containing composition with an isoosmolar osmolality is important in order to ensure a good biocompatibility. Many of the known cyclosporine emulsions are hyperosmolar in order to achieve a good penetration through the blood-brain barrier when such compositions are used e.g. in the treatment of stroke. However, cyclosporine emulsions of the invention may also be used in other important therapeutic areas such as, e.g., in connection with cardiac reperfusion injury and immunosuppression, where the use of a hyperosmolar composition may lead to unwanted entrance into the brain of specific metabolites, substances, blood components etc., which in turn may lead to toxic or adverse effects, all of which are unwanted.

The terms osmolarity, osmolality and tonicity are often used interchangeably. For specific definitions see Remington's Pharmaceutical Sciences, 18$^{th}$ Edition, Mack Publishing Company 1990, pages 1481-1498, which hereby is incorporated by reference.

A composition of the present invention may also be used in the treatment of traumatic brain injury, where the composition crosses the blood-brain barrier due to breaches therein caused by the brain injury itself and where there is thus no need for a hyperosmolar composition to breach the blood-brain barrier. An isoosmolar composition is highly preferable to a hyperosmolar composition in such indications.

Cyclosporine

The cyclosporine may be any therapeutically active cyclosporine or analogues and derivatives of cyclosporines. The cyclosporine may have immunosuppressive properties or non-immunosuppressive properties (NICAMs), or it may have any other known or unknown effect (e.g. for cardioprotection or neuroprotection of for treatment in cardiovascular diseases such as myocardial infarction, reperfusion, or in neurodegenerative diseases, brain injury, ischemia, trauma, etc. It is known that cyclosporines have protective effects on mitochondria, Preferred are cyclosporines that are suitable for use in immunosuppression. The cyclosporine may be a natural or synthetic cyclosporine. As it appears from the following several chiral carbon atoms are present. Thus, any of these forms—either alone or in any combination—that have therapeutic activity are encompassed by the term "cyclosporine".

In the Examples, the following cyclosporine has been employed:
INN: Ciclosporin
Chemical Names:
a) Cyclo[[(2S,3R,4R,6E)-3-hydroxy-4-methyl-2-(methylamino)-oct-6-enoyl]-L-2-aminobutanoyl-N-methylglycyl-N-methyl-L-leucyl-Lvalyl-N-methyl-L-leucyl-L-alanyl-D-alanyl-N-methyl-L-leucyl-Nmethyl-L-leucyl-N-methyl-L-valyl]
b) Cyclo[[(E)-(2S,3R,4R)-3-hydroxy-4-methyl-2-(methylamino)-6-octenoyl]-L-2-aminobutyryl-N-methylglycyl-N-methyl-L-leucyl-Lvalyl-N-methyl-L-leucyl-L-alanyl-D-alanyl-N-methyl-L-leucyl-Nmethyl-L-leucyl-N-methyl-L-valyl]
c) [R-[R*,R*-(E)]]-Cyclic(L-alanyl-D-alanyl-N-methyl-L-leucyl-Nmethyl-L-leucyl-N-methyl-L-valyl-3-hydroxy-N,4-dimethyl-L-2-amino-6-octenoyl-L-α-aminobutyryl-N-methylglycyl-N-methyl-Lleucyl-L-valyl-N-methyl-L-leucyl)

Other names: Ciclosporine (DCI)
Ciclosporina (DCI-E)
Compendial names: Ciclosporin (Ciclosporinum) (Ph. Eur.)
Cyclosporine (USP)
CAS number: 59865-13-3
Structural formula (see FIG. 1)
Molecular formula: $C_{62}H_{111}N_{11}O_{12}$
Relative molecular mass (Mr): 1202.61
Chirality: Ciclosporin is a molecule of natural origin that possesses
several chiral carbon atoms.
General Properties
Physical form: white or almost white powder
Solubility: soluble in acetone, ethanol, methanol, ether, chloroform and methylene chloride; slightly soluble in saturated hydrocarbons;
practically insoluble in water
Specific optical rotation: −185° to −193° (methanol)
Phosphatidylcholine Egg lecithin and/or soy lecithin, particularly egg lecithin, are preferred as suppliers of phosphatidylcholine, notably 3-sn-phosphatidyl choline or hydrogenated 3-sn-phosphatidyl choline. Lecithins with a content of more than 60% of 3-sn-phosphatidyl choline and/or partially hydrogenated 3-sn-phosphatidyl choline and/or hydrogenated 3-sn-phosphatidyl choline are above all suited.

Pharmaceutically Tolerable Salts of Fatty Acids

An alkali salt of a free fatty acid with 6 to 26 carbon atoms may be added to adjust the pH value or to facilitate the emulsification and homogenization process. The sodium and potassium salts of palmitic acid, palmitoleic acid, stearic acid, oleic acid, linoleic acid and linolenic acid are especially preferred. In a preferred embodiment sodium oleate is employed.

Isotonically/Isoosmolar Adjusting Substance

As seen from the examples herein, glycerol has been employed to adjust the osmolarity of the composition to isoosmolar. However, other substances like sorbitol, xylitol, sodium chloride, glucose may also prove to be suitable.

Natural Oils (Long Chain Triglycerides)

Soy-bean oil or safflower oil or combinations thereof may be employed as natural oils. In a preferred embodiment, soy-bean oil is employed.

MCT-Oils (Medium-Chain Triglycerides)

As it appears from the following, it seems that the presence of an MCT-oil is important in order to achieve the desired stability of the emulsion, notably with respect to the physical stability of the emulsion. Cyclosporine has a very good solubility in MCT-oil and MCT-oil thus contributes to avoid undesired precipitation of cyclosporine during storage.

Moreover, MCT-oils seem to have a beneficial effect on the brain, e.g., there are indications that it may be beneficial in the treatment of Alzheimer's disease and other condition where stabilization protection and support of mitochondrial function is important/needed. Mitochondria are present and produce energy in almost all cells in the body. Mitochondrial collapse may be associated with a variety of acute injuries, such as myocardial infarctions and traumatic brain injury and chronic diseases like amyotrophic lateral sclerosis, multiple sclerosis, and other neurological disorders. In myocardial infarctions, reperfusion of the blocked artery can cause reperfusion injury and extra damage and disability to the heart muscle, as well as increased mortality. Mitochondrial protection in heart muscle tissue may moderate the long-term impact of heart attacks.

A suitable MCT-oil is coconut oil, palm oil or a combination thereof.

Water

The water employed must have a quality suitable for parenteral products, such as water for injection (pharmacopoeia standard).

Manufacturing Method

A suitable method for manufacturing a composition of the invention appears in FIG. 2 and in the Examples herein.

Examples of Compositions According to the Invention

In all the compositions mentioned herein, the osmolarity is adjusted to the isoosmolar value of about 285 to about 305 mosm/l, preferably adjused to about 295 to about 300 mosm/l.

More specifically, a composition according to the invention contains:
A cyclosporine in a concentration range of from 1 to 15 g/l,
A phosphatidylcholine (e.g. egg lecithin) in a concentration range of from 5 to 25 g/l,
A pharmaceutically tolerable alkali salt of a free fatty acid (e.g. sodium oleate) in a concentration range of from 0.1 to 1 g/l,
Optionally, pH adjustment e.g. sodium hydroxide 1 M in a sufficient amount to reach a final pH value of the composition of from about 6 to about 8.8,
Glycerol in a concentration range of from 10 to 50 g/l,
A natural oil (long chain triglyceride) (e.g. soy bean oil) in a concentration range of from 50 to 150 g/l,
Medium chain triglyceride-oil in a concentration range of from 50 to 150 g/l, and
Water up to 1 liter.

In particular embodiments, a composition according to the invention contains:
A cyclosporine in a concentration range of from 1 to 15 g/l,
Egg lecithin in a concentration range of from 5 to 25 g/l,
A pharmaceutically tolerable alkali salt of a free fatty acid (e.g. sodium oleate) in a concentration range of from 0.1 to 1 g/l, Optionally, pH adjustment e.g. sodium hydroxide 1 M in a sufficient amount to reach a final pH value of the composition of from about 8 to about 8.8,
Glycerol in a concentration range of from 10 to 50 g/l,
A natural oil (long chain triglyceride) (e.g. soy bean oil) in a concentration range of from 50 to 150 g/l,
Medium chain triglyceride-oil in a concentration range of from 50 to 150 g/l, and
Water up to 1 liter.

A cyclosporine in a concentration range of from 1 to 15 g/l,
A phosphatidylcholin (e.g. egg lecithin) in a concentration range of from 5 to 25 g/l,
sodium oleate in a concentration range of from 0.1 to 1 g/l,
optionally, pH adjustment e.g. sodium hydroxide 1 M in a sufficient amount to reach a final pH value of the composition of from about 8 to about 8.8,
Glycerol in a concentration range of from 10 to 50 g/l,
A natural oil (long chain triglyceride) (e.g. soy bean oil) in a concentration range of from 50 to 150 g/l,
Medium chain triglyceride-oil in a concentration range of from 50 to 150 g/l, and
Water up to 1 liter.

A cyclosporine in a concentration range of from 1 to 15 g/l,
egg lecithin in a concentration range of from 5 to 25 g/l,
sodium oleate in a concentration range of from 0.1 to 1 g/l,
optionally, pH adjustment e.g. sodium hydroxide 1 M in a sufficient amount to reach a final pH value of the composition of from about 8 to about 8.8,
Glycerol in a concentration range of from 10 to 50 g/l,
A natural oil (long chain triglyceride) (e.g. soy bean oil) in a concentration range of from 50 to 150 g/l,
Medium chain triglyceride-oil in a concentration range of from 50 to 150 g/l, and
Water up to 1 liter.

A cyclosporine in a concentration range of from 1 to 15 g/l,
A phosphatidylcholin (e.g. egg lecithin) in a concentration range of from 5 to 25 g/l,
A pharmaceutically tolerable alkali salt of a free fatty acid (e.g. sodium oleate) in a concentration range of from 0.1 to 1 g/l,
Optionally, pH adjustment e.g. sodium hydroxide 1 M in a sufficient amount to reach a final pH value of the composition of from about 8 to about 8.8,
Glycerol in a concentration range of from 10 to 50 g/l,
soy bean oil in a concentration range of from 50 to 150 g/l,
Medium chain triglyceride-oil in a concentration range of from 50 to 150 g/l, and
Water up to 1 liter.

A cyclosporine in a concentration range of from 1 to 15 g/l,
egg lecithin in a concentration range of from 5 to 25 g/l,
A pharmaceutically tolerable alkali salt of a free fatty acid (e.g. sodium oleate) in a concentration range of from 0.1 to 1 g/l,
Optionally, pH adjustment e.g. sodium hydroxide 1 M in a sufficient amount to reach a final pH value of the composition of from about 8 to about 8.8,
Glycerol in a concentration range of from 10 to 50 g/l,
soy bean oil in a concentration range of from 50 to 150 g/l,
Medium chain triglyceride-oil in a concentration range of from 50 to 150 g/l, and
Water up to 1 liter.

A cyclosporine in a concentration range of from 1 to 15 g/l,
A phosphatidylcholin (e.g. egg lecithin) in a concentration range of from 5 to 25 g/l,
sodium oleate in a concentration range of from 0.1 to 1 g/l,
optionally, pH adjustment e.g. sodium hydroxide 1 M in a sufficient amount to reach a final pH value of the composition of from about 8 to about 8.8,
Glycerol in a concentration range of from 10 to 50 g/l,
soy bean oil in a concentration range of from 50 to 150 g/l,
Medium chain triglyceride-oil in a concentration range of from 50 to 150 g/l, and
Water up to 1 liter.

A cyclosporine in a concentration range of from 1 to 15 g/l,
egg lecithin in a concentration range of from 5 to 25 g/l,
sodium oleate in a concentration range of from 0.1 to 1 g/l,
optionally, pH adjustment e.g. sodium hydroxide 1 M in a sufficient amount to reach a final pH value of the composition of from about 8 to about 8.8,
Glycerol in a concentration range of from 10 to 50 g/l,
soy bean oil in a concentration range of from 50 to 150 g/l,
Medium chain triglyceride-oil in a concentration range of from 50 to 150 g/l, and
Water up to 1 liter.

Moreover, the invention relates to compositions having the following compositions:
A cyclosporine in a concentration of 5 g/l,
A phosphatidylcholin (e.g. egg lecithin) in a concentration of 12 g/l,
A pharmaceutically tolerable alkali salt of a free fatty acid (e.g. sodium oleate) in a concentration of 0.3 g/l,
Optionally, pH adjustment e.g. sodium hydroxide 1 M in a sufficient amount to reach a final pH value of the composition of from about 8 to about 8.8,
Glycerol in a concentration of 25 g/l,
A natural oil (long chain triglyceride) (e.g. soy bean oil) in a concentration of 100 g/l,
Medium chain triglyceride-oil in a concentration range of 100 g/l,
Water up to 1 liter.

A cyclosporine in a concentration of 5 g/l,
egg lecithin in a concentration of 12 g/l,
A pharmaceutically tolerable alkali salt of a free fatty acid (e.g. sodium oleate) in a concentration of 0.3 g/l,
Optionally, pH adjustment e.g. sodium hydroxide 1 M in a sufficient amount to reach a final pH value of the composition of from about 8 to about 8.8,
Glycerol in a concentration of 25 g/l,
A natural oil (long chain triglyceride) (e.g. soy bean oil) in a concentration of 100 g/l,
Medium chain triglyceride-oil in a concentration range of 100 g/l,
Water up to 1 liter.

A cyclosporine in a concentration of 5 g/l,
A phosphatidylcholin (e.g. egg lecithin) in a concentration of 12 g/l,
sodium oleate in a concentration of 0.3 g/l,
Optionally, pH adjustment e.g. sodium hydroxide 1 M in a sufficient amount to reach a final pH value of the composition of from about 8 to about 8.8,
Glycerol in a concentration of 25 g/l,
A natural oil (long chain triglyceride) (e.g. soy bean oil) in a concentration of 100 g/l,
Medium chain triglyceride-oil in a concentration range of 100 g/l,
Water up to 1 liter.

A cyclosporine in a concentration of 5 g/l,
egg lecithin in a concentration of 12 g/l,
sodium oleate in a concentration of 0.3 g/l,
Optionally, pH adjustment e.g. sodium hydroxide 1 M in a sufficient amount to reach a final pH value of the composition of from about 8 to about 8.8, Glycerol in a concentration of 25 g/l,
A natural oil (long chain triglyceride) (e.g. soy bean oil) in a concentration of 100 g/l,
Medium chain triglyceride-oil in a concentration range of 100 g/l,
Water up to 1 liter.
A cyclosporine in a concentration of 5 g/l,
A phosphatidylcholin (e.g. egg lecithin) in a concentration of 12 g/l,
A pharmaceutically tolerable alkali salt of a free fatty acid (e.g. sodium oleate) in a concentration of 0.3 g/l,
Optionally, pH adjustment e.g. sodium hydroxide 1 M in a sufficient amount to reach a final pH value of the composition of from about 8 to about 8.8,
Glycerol in a concentration of 25 g/l,
soy bean oil in a concentration of 100 g/l,
Medium chain triglyceride-oil in a concentration range of 100 g/l,
Water up to 1 liter.
A cyclosporine in a concentration of 5 g/l,
egg lecithin in a concentration of 12 g/l,
A pharmaceutically tolerable alkali salt of a free fatty acid (e.g. sodium oleate) in a concentration of 0.3 g/l,
Optionally, pH adjustment e.g. sodium hydroxide 1 M in a sufficient amount to reach a final pH value of the composition of from about 8 to about 8.8,
Glycerol in a concentration of 25 g/l,
soy bean oil in a concentration of 100 g/l,
Medium chain triglyceride-oil in a concentration range of 100 g/l,
Water up to 1 liter.
A cyclosporine in a concentration of 5 g/l,
A phosphatidylcholin (e.g. egg lecithin) in a concentration of 12 g/l,
sodium oleate in a concentration of 0.3 g/l,
Optionally, pH adjustment e.g. sodium hydroxide 1 M in a sufficient amount to reach a final pH value of the composition of from about 8 to about 8.8,
Glycerol in a concentration of 25 g/l,
soy bean oil in a concentration of 100 g/l,
Medium chain triglyceride-oil in a concentration range of 100 g/l,
Water up to 1 liter.
A cyclosporine in a concentration of 5 g/l,
egg lecithin in a concentration of 12 g/l,
sodium oleate in a concentration of 0.3 g/l,
Optionally, pH adjustment e.g. sodium hydroxide 1 M in a sufficient amount to reach a final pH value of the composition of from about 8 to about 8.8,
Glycerol in a concentration of 25 g/l,
soy bean oil in a concentration of 100 g/l,
Medium chain triglyceride-oil in a concentration range of 100 g/l,
Water up to 1 liter.

In all the above-mentioned compositions, the medium chain triglycerides may be coconut oil, palm oil, or combinations thereof.

The composition of the emulsion that has been tested in a clinical study was produced according to the following formula (300 L batch size):

| Ingredient | Quantity (kg) | Quality standard |
| --- | --- | --- |
| Cyclosporine | 1.50 | R1-CEP 1999-034 Rev 02 |
| Egg lechithin | 3.60 | |
| Glycerol (water free) | 7.50 | Ph. Eur. |
| Sodium oleate | 0.09 | |
| Sodium hydroxide 1M | q.s. | Ph. Eur. |
| Soya-bean oil (long chain triglyceride) | 30.00 | Ph. Eur. |
| MCT-oil (medium chain triglyceride) | 30.00 | Ph. Eur. |
| Water for injection | Ad 300 L | Ph. Eur. |
| Nitrogen gas | As required | Ph. Eur./USP |

Thus, a preferred composition of the invention is the following:

| Ingredient | Concentration g/L |
| --- | --- |
| Cyclosporine | 5 |
| Egg lechithin | 12 |
| Glycerol (water free) | 25 |
| Sodium oleate | 0.3 |
| Sodium hydroxide 1M | q.s. |
| Soya-bean oil (long chain triglyceride) | 100 |
| MCT-oil (medium chain triglyceride) | 100 |
| Water for injection | Ad 1 L |
| Nitrogen gas | As required (for production purposes) |

The MCT-oil is coconut oil, palm oil or a combination thereof.

As it appears from the experimental section a composition according to the invention, notably, the above-mentioned composition is bioequivalent to the SANDIMMUNE® product, i.e. the concentrate diluted to a ready-to-use composition. The bioequivalence study has been carried out according to well-established guidelines (EMEA—European Medicines Agency, London, January 2010. Guideline on the investigation of bioequivalence, or US Department of Health and Human Services, Food and Drug Administration, March 2003, Guidance for Industry, Bioavailability and Bioequivalence Studies for Orally Administered Drug Product—General Considerations).

The study also reveals that a composition according to the invention has a much better safety profile than the SANDIMMUNE® product. Thus, without premedication with corticosteroids, in 19 subjects two severe anaphylactic reactions were observed after administration with SANDIMMUNE®, whereas no such reactions were observed after administration in 33 subjects with a composition according to the invention. To sum up from the clinical study the following table shows the adverse effects observed. Two serious adverse events (SAEs) were reported. These were anaphylactic and anaphylactoid reactions that occurred after administration of SANDIMMUNE® injection. The proportion of overall adverse effects was significantly higher in the SANDIMMUNE® injection compared to the composition according to the invention.

|  | Proportion Sandimmune injection | Proportion CicloMulsion (according to the invention) | Mean Ratio (%) | 95% Confidence Interval of Ratio (%) | McNemar's p-value |
|---|---|---|---|---|---|
| Overall | 0.800 | 0.350 | −0.450 | −0.668; −0.232 | 0.0027 |
| Eye disorders | 0.050 | 0.000 | −0.050 | −0.146; 0.046 | N/C |
| Gastrointestinal disorders | 0.150 | 0.150 | 0.000 | −0.139; 0.139 | 1.0000 |
| Immune system disorders | 0.200 | 0.050 | −0.150 | −0.306; 0.006 | 0.0833 |
| Anaphylactic reaction | 0.050 | 0.000 | −0.050 | −0.146; 0.046 | N/C |
| Anaphylactoid reaction | 0.050 | 0.000 | −0.050 | −0.146; 0.046 | N/C |
| Hypersensitivity | 0.100 | 0.050 | −0.050 | −0.146; 0.046 | 0.3173 |
| Nervous system disorders | 0.500 | 0.250 | −0.250 | −0.485; −0.015 | 0.0588 |
| Psychiatric disorders | 0.050 | 0.000 | −0.050 | −0.146; 0.046 | N/C |
| Reproductive system and breast disorders | 0.050 | 0.000 | −0.050 | −0.146; 0.046 | N/C |
| Respiratory, thoracic and mediastinal disorders | 0.050 | 0.050 | 0.000 | 0.000; 0.000 | N/C |
| Vascular Disorders | 0.400 | 0.100 | −0.300 | −0.544; −0.056 | 0.0339 |

Another advantage of a composition of the invention (besides bioequivalence with SANDIMMUNE® injection and better safety profile than the SANDIMMUNE® injection) is the excellent stability of the composition. It is currently believed that the presence of medium-chain triglycerides plays an important role in this respect. Thus, based on stability studies carried out according to ICH guidelines and reported in the Examples, the overall conclusion is that a shelf-life of 30-36 months when stored below 25° C. and protected from light is reasonable.

Other Advantages are:
1. Ready-to-use solution. SANDIMMUNE® injection is marketed as a 50 mg/ml infusion concentrate that has to be drawn up by a syringe and then injected into a larger volume of saline or 5% glucose. The concentrate solution is highly viscous, especially at room temperature or below, which makes it more difficult to extract and empty to the right amount than with a ready-to-use composition. Further, following injection of the infusion concentrate into saline, careful mixing is required to avoid injection of large cyclosporine-containing CREMOPHOR® lumps into the circulation, which also affects the concentration of cyclosporine given early and late in a treatment.
2. No un-physiological emulsifier. The contents of a composition of the invention are physiological fats and phospholipids that can be metabolized by the human body.
3. No risk of solvent-related severe hypersensitivity reactions, including anaphylactic reactions and death.
4. No risk of solvent-related cyto-, nephro- or cardiotoxicity.
5. Eliminates the need for specialized IV tubing required for CREMOPHOR®-containing products (to prevent leaching of plasticizers).
6. Premedication with corticosteroids or antihistamines is not necessary.
7. No risk of penetration of unwanted substance over the blood-brain barrier.

The emulsions of the invention are suitable to use in the treatment of disease where cyclosporine is indicated. Examples are immunosuppresive disorders, reperfusion injury (organ damage), cardiac reperfusion injury (cardioprotection), kidney reperfusion injury (nephroprotection), liver reperfusion injury (hepatoprotection), prevention of brain damage (neuroprotection).

BRIEF DESCRIPTION OF THE DRAWINGS

Legend to Figures

FIGS. 5A-5B show a summary of a clinical study to compare the bioavailability and pharmacokinetics of cyclosporine (Example 4).

DETAILED DESCRIPTION OF THE PREFERRED EMBODIMENTS

Figure 1:
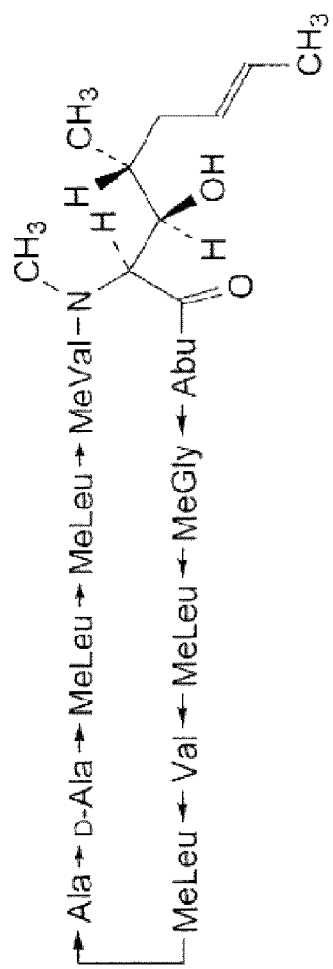
FIG. 1 shows the structure of cyclosporine
Figure 2:
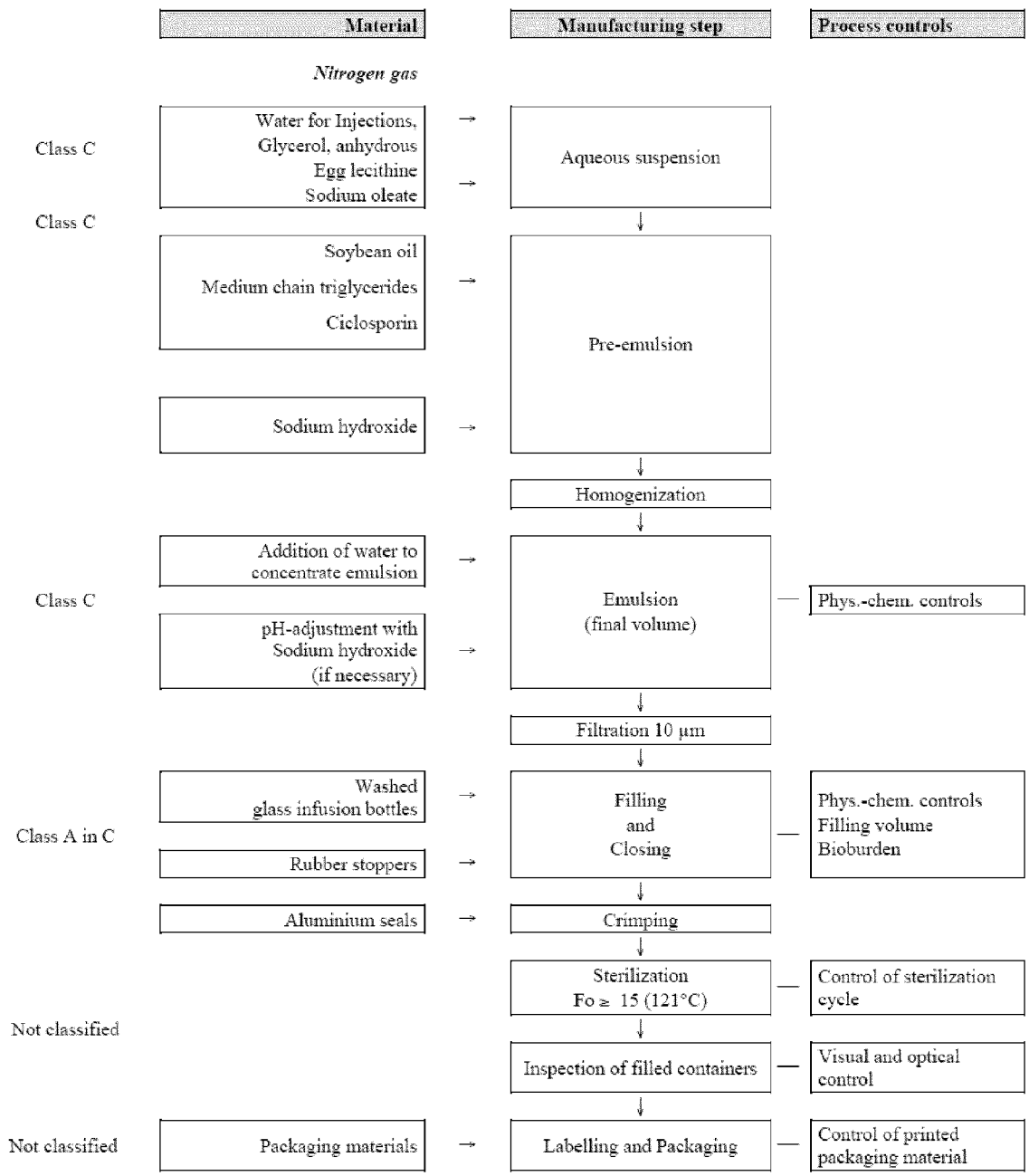
FIG. 2 shows a method for the manufacture of an emulsion according to the invention
Figure 3:
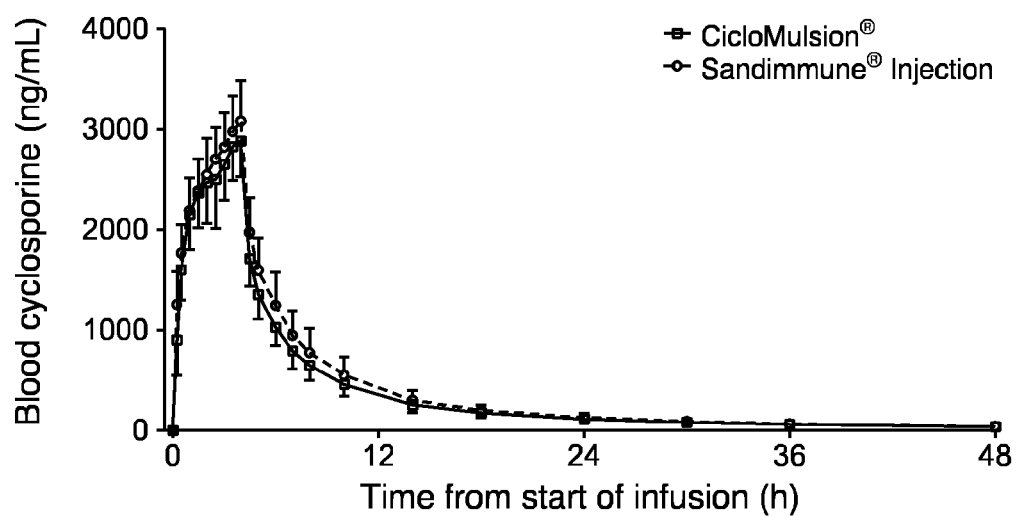
FIG. 3 shows arithmetic means with standard deviation of blood Cyclosporine concentration in participants administered CicloMulsion or Sandimmune. n=52

The invention is further illustrated in the following non-limiting examples.

EXAMPLES

Example 1

Manufacturing of a Composition According to the Invention

Preparation of the Emulsion
Preparation of Aqueous Suspension:

A mixing tank is provided with the appropriate quantity of hot water for injection. All raw materials except the oil components are ground and dispersed in water for injection at 55-70° C. The suspension is dispersed by means of intense mixing.

Preparation of Pre-Emulsion:

A solution of pre-heated oil components (50-60° C.) containing dissolved cyclosporine is added. Aqueous suspension and oil phase are mixed at 55-70° C. If necessary, pH adjustment.

Homogenization:

The preparation of the final emulsion takes place by several homogenization steps. Pressures of 400±30 bar (stage 1) and 100±30 bar (stage 2) are applied. The temperature of the emulsion is between 55° C. and 90° C. Between the homogenization steps the emulsion is stored in intermediate storage tanks Final Emulsion:

Depending on the capacity of the used equipment (homogenizers and vessel) the emulsion has to be diluted under stirring with the appropriate amount of water for injection. The resulting emulsion is cooled down to a temperature of 15-25° C. A sample of the final concentration is taken for in-process control and a pH-adjustment may be carried out.

Filtration of the Emulsion:

The emulsion is filtered through a 10 μm absolute pore size filter.

Filling and Closing:

The emulsion is filled under a nitrogen atmosphere into suitable infusion bottles. Filled bottles are closed with rubber stoppers and aluminium caps with transparent flip-off caps.

Sterilization:

The filled containers are sterilized in a rotating autoclave.

Example 2

Composition According to the Invention

The composition of the emulsion that has been tested in a clinical study was produced according to the following formula (300 L batch size):

| Ingredient | Quantity (kg) | Quality standard |
|---|---|---|
| Cyclosporine | 1.50 | R1-CEP 1999-034 Rev 02 |
| Egg lecithin | 3.60 | |
| Glycerol (water free) | 7.50 | Ph. Eur. |
| Sodium oleate | 0.09 | |
| Sodium hydroxide 1M | q.s. | Ph. Eur. |
| Soya-bean oil (long chain triglyceride) | 30.00 | Ph. Eur. |
| MCT-oil (medium chain triglyceride) | 30.00 | Ph. Eur. |
| Water for injection | Ad 300 L | Ph. Eur. |
| Nitrogen gas | As required | Ph. Eur./USP |

Example 3

Stability of a Composition According to the Invention

The composition of Example 2 was subjected to stability studies in accordance with the ICH guidelines.

The Ciclosporin 5 mg/ml Emulsion for Injection batch PP0915013 is put on stability at 25° C./60% RH and 40° C./75% RH in accordance with ICH requirements. Currently 12 months data are available.

All results, at both temperatures, are well within specifications. The cyclosporine appears very stable with no decreasing trend. Only small amounts of degradation products are found. The following tables summaries the results.

| | 25° C./60% RH | | | | |
|---|---|---|---|---|---|
| | Storage time (Months) | | | | |
| Test item | 0 | 3 | 6 | 9 | 12 |
| Appearance White homogeneous emulsion | conforms | conforms | conforms | conforms | conforms |
| pH 6.0-8.5 | 8.4 | 7.8 | 7.6 | 7.3 | 7.2 |
| Particle size distribution >1 μm 100% ≤5 μm 98% ≤1.5 μm | 100/100 | 100/98.6 | 100/99.2 | 100/99 | 100/98 |
| Particle size distribution <1 μm | | | | | |
| z-average ≤350 nm | 240 | 243 | 239 | 239 | 239 |
| Polydispersion ≤0.25 | 0.09 | 0.06 | 0.08 | 0.09 | 0.08 |
| Peroxide value ≤2.5 mEq/L | 0.02 | 0.04 | 0.05 | 0.10 | 0.0 |
| Ciclosporin assay 95.0-105.0% | 97.6 | 100.6 | 100.2 | 100.2 | 101.4 |

-continued

25° C./60% RH

| Test item | Storage time (Months) | | | | |
|---|---|---|---|---|---|
| | 0 | 3 | 6 | 9 | 12 |
| Degradation products | | | | | |
| ciclosporin H (≤1.4%) | <DL | 0.1 | 0.3 | 0.2 | 0.3 |
| dihydrociclosporin A (≤1.4%) | 0.1 | 0.1 | 0.3 | 0.2 | 0.2 |
| isociclosporin A (≤1.4%) | 0.1 | 0.2 | 0.1 | 0.2 | 0.1 |
| single unknown (≤0.2%) | 0.1 | 0.1 | 0.1 | <DL | 0.1 |
| Total (≤2.0%) | <0.4 | <0.5 | <0.8 | <0.7 | <0.8 |
| Free fatty acids ≤12 mEg/L | 2 | 2 | 3 | 3 | 4 |
| Lysophosphatidylcholine ≤16.7% | 3 | 6 | 7 | 7 | 8 |
| Sterility Sterile | sterile | — | — | — | — |

40° C./75% RH

| Test item | Storage time (Months) | | |
|---|---|---|---|
| | 0 | 3 | 6 |
| Appearance White homogeneous emulsion | conforms | conforms | conforms |
| pH 6.0-8.5 | 8.4 | 7.2 | 6.5 |
| Particle size distribution >1 μm 100% ≤5 μm 98% ≤1.5 μm | 100/100 | 100/99.6 | 100/99.6 |
| Particle size distribution <1 μm | | | |
| z-average ≤350 nm | 240 | 242 | 240 |
| Polydispersion ≤0.25 | 0.09 | 0.05 | 0.05 |
| Peroxide value ≤2.5 mEq/L | 0.02 | 0.06 | 0.08 |
| Ciclosporin assay 95.0-105.0% | 97.6 | 101.2 | 99.6 |
| Degradation products | | | |
| ciclosporin H (≤1.4%) | <DL | 0.4 | 0.9 |
| dihydrociclosporin A (≤1.4%) | 0.1 | 0.1 | 0.3 |
| isociclosporin A (≤1.4%) | 0.1 | 0.2 | 0.1 |
| single unknown (≤0.2%) | 0.1 | 0.1 | 0.1 |
| Total (≤2.0%) | <0.4 | <0.7 | <1.3 |
| Free fatty acids ≤12 mEg/L | 2 | 4 | 6 |
| Lysophosphatidylcholine ≤16.7% | 3 | 9 | 12 |
| Sterility Sterile | sterile | — | — |

Example 4

A clinical study to compare the bioavailability and pharmacokinetics of cyclosporine

SUMMARY

Background: Ciclosporin is a widely used immunosuppressant in organ and tissue transplantation. Ciclosporin has poor solubility in water, and the concentrate for solution for infusion has therefore been formulated in polyoxyethylated castor oil (Cremophor EL®). However, intravenous administration of ciclosporin preparations containing cremophor has been associated with hypersensitivity reactions, with responses ranging from mild skin conditions to anaphylaxis and cardiac collapse. A cremophor-free, ready-to-use cidosporin lipid emulsion (CicloMulsion, ciclosporin 5 mg/ml) for intravenous use has been developed. The objectives of the present study were to compare the pharmacokinetics and tolerability profile of CicloMulsion with the reference product Sandimmune Injection.

Methods: Healthy, male and female, Caucasian and non-Caucasian volunteers (n=52), were investigated according to an open-label, laboratory-blind, subject-blind, randomized, single-dose, two-period cross-over design. Five mg/kg of each of the two formulations was intravenously infused over 4 hours. Blood concentrations of ciclosporin were determined by validated LC-MS/MS analysis. FDA and EMA-compliant standard pharmacokinetic comparisons were performed using analysis of variance. Point estimates and 90% confidence intervals for the test/reference geometric least square mean ratios of relevant variables were calculated. Tolerability and safety were evaluated by adverse event monitoring, full blood count, vital signs measurements. electrocardiogram and post-study physical examination.

Figure 5A:
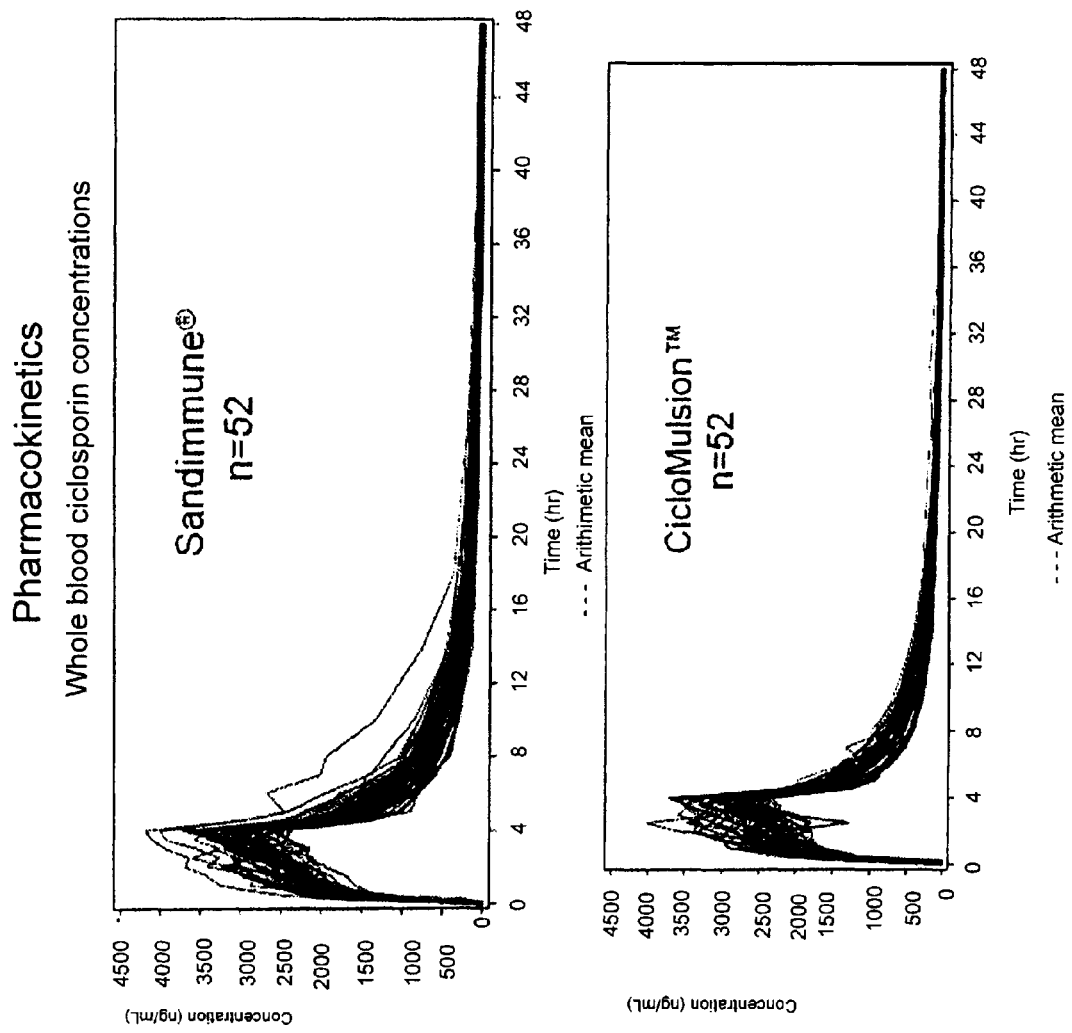
FIG. 5A shows results from combined individual graphs of whole blood concentrations following infusion of 5 mg/kg ciclosporin sampled over 48 hours in 52 healthy individuals, as described in Example 4 (Top—Sandimmune Injection; Bottom—CicloMulsion).
Figure 5B:
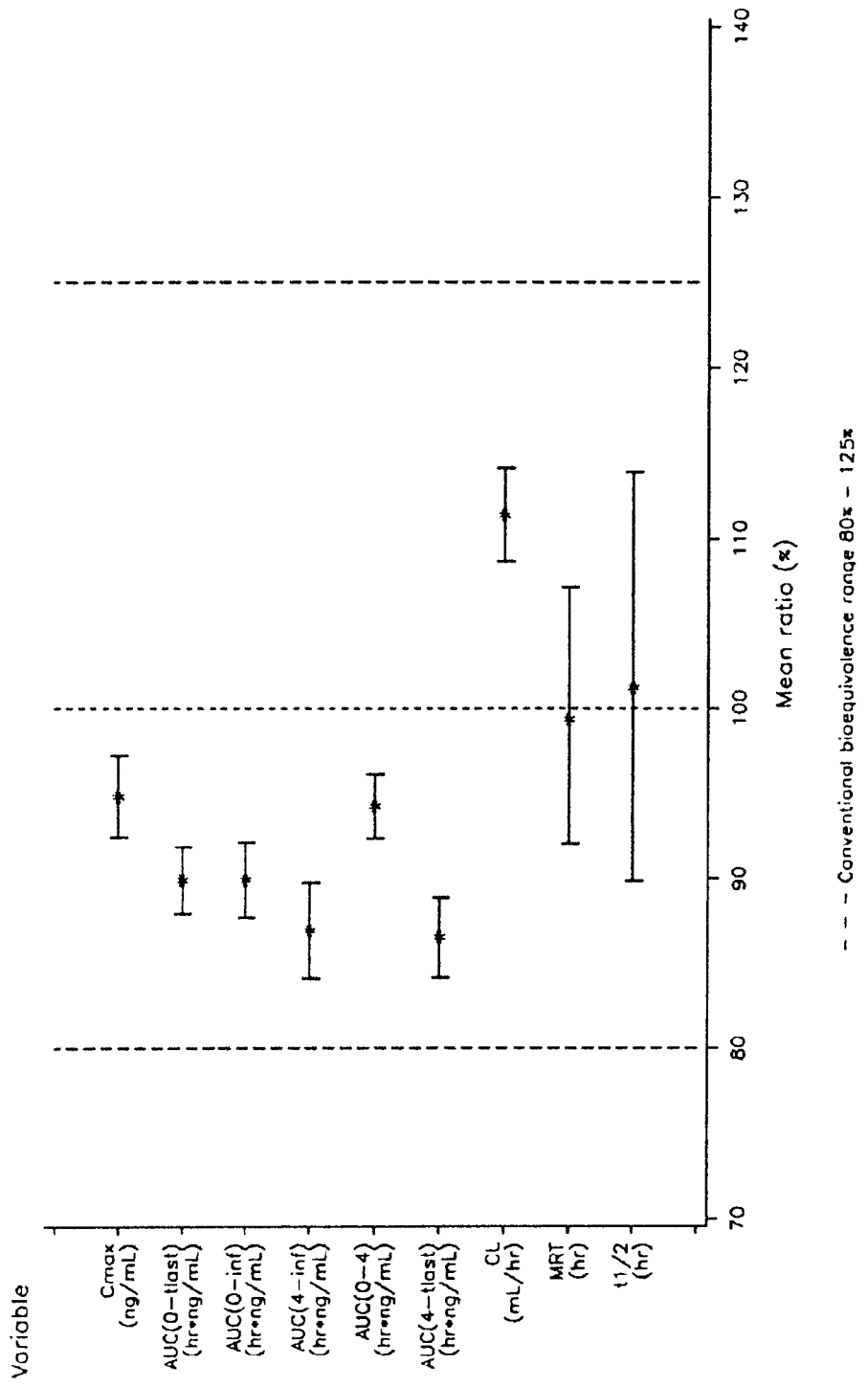

Results: FIG. 5A shows the combined individual graphs of whole blood concentrations following infusion of 5 mg/kg ciclosporin sampled over 48 hours in 52 healthy individuals. (Top—Sandimmune Injection; Bottom—CicloMulsion). Table 1 and FIG. 5B show the confidence interval (90%) for the mean ratios (%) of CicloMulsion/Sandimmune) and intraindividual coefficient of variation (CV) of whole blood ciclosporin pharmacokinetic variables. As reflected in Table 2, two serious adverse events (SAEs) were reported. These were the anaphylactic and anaphylactoid reactions that occurred after administration of Sandimmune Injection. The proportion of overall adverse events was significantly higher in the Sandimmune Injection compared to CicloMulsion.

TABLE 1

| Variable | Mean Ratio (%) | 90% Confidence Interval of Ratio | Intra-individual CV (%) | Power |
|---|---|---|---|---|
| $C_{max}$(ng/mL) | 94.80 | (92.43;97.23) | 7.70 | >99% |
| AUC(0-$t_{last}$)(hr*ng/mL) | 89.88 | (87.92;91.88) | 6.71 | >99% |
| AUC(0-∞) (hr*ng/mL) | 89.91 | (87.71;92.16) | 7.53 | >99% |
| AUC(4-∞(hr*ng/mL) | 86.90 | (84.12;89.77) | 9.91 | >99% |
| AUC(0-4) (hr*ng/mL) | 94.23 | (92.37;96.14) | 6.08 | >99% |
| AUC(4-$t_{last}$)(hr*ng/mL) | 86.52 | (84.20;88.90) | 8.27 | >99% |
| CL (mL/hr) | 111.38 | (108.67;114.15) | 7.49 | >99% |
| MRT (hr) | 99.33 | (92.08;107.14) | 23.36 | >99% |
| $t_{1/2z}$ (hr) | 101.19 | (89.88;113.93) | 37.28 | >93% |

TABLE 2

|  | Proportion | | | 95% | |
| --- | --- | --- | --- | --- | --- |
|  | Sandimmune - Injection | Ciclo-Mul-sion ™ | Mean Ratio (%) | Confidence Interval of Ratio (%) | McNemar's p-value |
| Overall | 0.800 | 0.350 | −0.450 | −0.668; −0.232 | 0.0027 |
| Eye Disorders | 0.050 | 0.000 | −0.050 | −0.146; 0.046 | N/C |
| Gastrointestinal disorders | 0.150 | 0.150 | 0.000 | −0.139; 0.139 | 1.0000 |
| Immune system disorders | 0.200 | 0.050 | −0.150 | −0.306; 0.006 | 0.0833 |
| Anaphylactic reaction | 0.050 | 0.000 | −0.050 | −0.146; 0.046 | N/C |
| Anaphylactoid reaction | 0.050 | 0.000 | −0.050 | −0.146; 0.046 | N/C |
| Hypersensitivity | 0.100 | 0.050 | −0.050 | −0.146; 0.046 | 0.3173 |
| Nervous system disorders | 0.500 | 0.250 | −0.250 | −0.485; 0.015 | 0.0588 |
| Psychiatric disorders | 0.050 | 0.000 | −0.050 | −0.146; 0.046 | N/C |
| Reproductive system and breast disorders | 0.050 | 0.000 | −0.050 | −0.146; 0.046 | N/C |
| Respiratory, thoracic and mediastinal disorders | 0.050 | 0.050 | 0.000 | 0.000; 0.000 | N/C |
| Vascular Disorders | 0.400 | 0.100 | −0.300 | −0.544; −0.056 | 0.0339 |

Conclusions:

CicloMulsion, a ready-to-use cremophor-free intravenous formulation of ciclosporin, is bioequivalent to Sandimmune Injection.

CicloMulsion displays an improved safety and tolerability profile.

Cremophor-related severe hypersensitivity reactions, including anaphylactic reactions and death, can thus be avoided in patients requiring intravenous ciclospurin.

CicloMulsion has the following advantages over i.v. Sandimmune Injection:
1. Ready-to-use solution
2. Physiological emulsifier. The contents of CicloMulsion are hysiological fats and phospholipids that can be metabolized by the human body.
3. No risk of cremophor-related severe hypersensitivity reactions, including anaphylactic reactions and death.
4. No risk of cremophor-related cyto-, nephro- or cardiotoxicity.
5. Eliminates need for specialized i.v. tubing required for cremophor-containing products (to prevent leaching of plasticizers).

Details Regarding the Clinical Study

Introduction

Cyclosporine is widely used to prevent rejection of grafts after transplantation. The intravenous formulation currently on the market, SANDIMMUNE® Injection (Sandimmune), uses CREMOPHOR® EL (CrEL) as emulsifying excipient. CrEL is known to cause hypersensitivity reactions in some patients, ranging from skin reactions to anaphylactic shock and death. We have assessed the pharmacokinetics and tolerability of a new, CrEL-free lipid emulsion of cyclosporine, CICLOMULSION®, compared to Sandimmune. Fifty-two healthy subjects were treated with 5 mg/kg of each of the two formulations of cyclosporine as 4 h intravenous infusion. Bioequivalence assessments according to current guidelines were performed. The geometric mean ratios for CicloMulsion/Sandimmune (90% confidence interval) were 0.90 (0.88-0.92) for Area Under Curve (0 h to the last quantifiable concentration) and 0.95 (0.92-0.97) for maximum blood cyclosporine concentration. For all additional variables analyzed, the 90% confidence intervals were also within the accepted bioequivalence range of 0.80-1.25. One anaphylactoid and one anaphylactic reaction, both classified as serious adverse events, were reported after treatment with Sandimmune. No serious adverse events were recorded after treatment with CicloMulsion. The proportion of overall adverse events was significantly higher for Sandimmune. We conclude that CicloMulsion is bioequivalent to Sandimmune and exhibits fewer adverse reactions.

LIST OF ABBREVIATIONS

AE Adverse Event
ANOVA Analysis of variance
AUC Area Under Curve
$AUC_{0-4}$ Area Under Curve for time 0 to 4 hours
$AUC_{0-t}$ Area Under Curve for time 0 to the last quantifiable concentration
$AUC_{0-\infty}$ Area Under Curve for time 0 hours extrapolated to infinity
$AUC_{4-t}$ Area Under Curve for time 4 to the last quantifiable concentration
$AUC_{4-\infty}$ Area Under Curve for time 4 hours extrapolated to infinity
CI Confidence Interval
CL Clearance
$C_{max}$ Maximum blood concentration
CicloMulsion Cremophor EL-free cyclosporine lipid emulsion
CrEL Cremophor EL
CsA Cyclosporine, Ciclosporin, Cyclosporin A
CV Coefficient of variation
ECG Electrocardiogram
EDTA Ethylenediaminetetraacetic acid
EMA European Medicines Agency
FDA Food and Drug Administration
IV Intravenous
LC-MS/MS Liquid chromatography-mass spectrometry/mass spectrometry
LLOQ Lower level of quantification
MedDRA Medical Dictionary for Regulatory Activities
MRT Mean Residence Time
Ph Eur European Pharmacopoeia
PVC Polyvinyl chloride
SAE Serious Adverse Event
Sandimmune SANDIMMUNE® Injection
$SpO_2$ Peripheral Blood Oxygen Saturation
$t_{1/2,z}$ Apparent terminal half-life
USP United States Pharmacopeia Cyclosporine (CsA) is a potent immunosuppressant first registered in 1983 that acts by reducing the function of T-lymphocytes through inhibition of calcineurin. CsA is widely used to prevent organ rejection and graft-versus-host disease after solid organ or bone marrow transplantation, and to treat autoimmune conditions such as psoriasis, atopic dermatitis, pyoderma gangrenosum, ulcerative colitis, idiopathic nephrotic syndrome and inflammatory uveitis (1-7). The molecule is highly hydrophobic and requires a lipophilic solvent for administration. The intravenous (IV) form of CsA currently on the market, SANDIMMUNE® Injection (Novartis Pharma Stein AG, Switzerland) (Sandimmune), is a preparation with ethanol and polyoxyethylated castor oil, CREMOPHOR® EL (CrEL).

CrEL is not inert (8) and there have been a number of reports of serious adverse effects after administration of IV CsA due to reactions to this carrier medium (9-16). Hypersensitivity reactions to CrEL have also been reported when used for other intravenous preparations of drugs such as diazepam and ALTHESIN® (17-21). In rodents, neurotoxicity, cardiotoxicity and nefrotoxicity due to IV CsA dissolved in CrEL have been demonstrated (22-25) and, in a canine model, CrEL has been shown to reduce cardiac output and hepatic blood flow in a non-dose-dependent fashion (26). The effects of CrEL include complement activation, histamine release and severe hypersensitivity reactions (8, 17, 19, 21).

CsA in CrEL requires a dilution step prior to administration. Improper preparation of CrEL-containing formulations has been reported to cause anaphylactoid reactions (27, 28). An additional concern with the use of ethanol and CrEL is the leaching of plasticizers from polyvinyl chloride (PVC) bags and infusion sets used in routine clinical practice. Consequently, preparation and administration should be done using glass or other non-PVC infusion sets (29, 30).

Concern about the safety of CrEL as a carrier medium for IV drugs has been raised on numerous occasions and several drugs that previously were produced in preparations with CrEL are now available only with other carrying media such as lipid emulsions. Known examples are propofol (17, 31) and diazepam (32). Others, such as the chemotherapeutic agent paclitaxel, are available both with and without CrEL as solvent (33), and the anesthetic drug ALTHESIN® that contained CrEL is no longer marketed for use in humans (17, 21, 34).

In this study, the objective was to assess the pharmacokinetics of a novel CrEL- and ethanol-free ready-to-use preparation of CsA for IV administration, CICLOMULSION® (NeuroVive Pharmaceutical AB, Lund, Sweden), in relation to the CrEL-containing product currently on the market (SANDIMMUNE® Injection) and to assess whether the two formulations are bioequivalent. A ready-to-use preparation without CrEL potentially offers increased patient safety with fewer adverse events due to improper handling or immunological reactions to CrEL.

Study Design

This was a single-center, open-label, subject-blind, laboratory-blind, single-dose, randomized, two-treatment, two-period, two-sequence crossover study of the pharmacokinetics of two formulations of IV CsA. The primary objective was to assess the pharmacokinetics, and the secondary objective to compare the tolerability profiles of the two preparations.

The study protocol, including amendments, subject information sheets and informed consent documents, were reviewed by the Ethics Committee of the Faculty of Health Sciences of the University of the Free State (Reference number ETOVS 65/09), and by the South African Medicines Control Council (Reference number BE 2009009), and written approval was acquired. The study was performed in accordance with the declaration of Helsinki and Guideline for Good Clinical Practice issued by the International Conference on Harmonization. It was designed to comply with the Guidance for Industry—Statistical Approaches to Establishing Bioequivalence issued by the United States Department of Health and Human Services, Food and Drug Administration (FDA) (35), and the Note for Guidance on the Investigation of Bioavailability and Bioequivalence by The European Medicines Agency (EMA) (36).

Cyclosporine Formulations

The reference formulation of CsA used was SANDIMMUNE® Injection (Novartis Pharma Stein AG, Switzerland, 50 mg/mL CsA, United States Pharmacopeia, USP) (approved under U.S. New Drug Application Number 050573) containing CREMOPHOR® EL (each 1 mL infusion concentrate was diluted in 20 mL 0.9% saline solution prior to use). The test product used was CICLOMULSION® (NeuroVive Pharmaceutical AB, Lund, Sweden) 5 mg/mL ready-to-use Cremophor- and ethanol-free cyclosporine Ph Eur/USP lipid emulsion. Each mL of the lipid emulsion contains 100 mg of refined soya-bean oil, 100 mg medium-chain triglycerides, 12 mg egg lecithin, 25 mg glycerol, water, and sodium oleate and sodium hydroxide for pH adjustment.

Participants

Healthy male and healthy, non-pregnant, non-lactating female volunteers between 18 and 55 years of age with a body mass index within the range of 19-33 $kg/m^2$ were eligible. Further inclusion criteria were body mass 60-100 kg, normal 12-lead electrocardiogram (ECG) and vital signs, clinically acceptable findings in medical history and physical examinations, laboratory results within the reference ranges (unless the deviation was considered irrelevant for the purpose of the study), willingness to undergo pre-, interim- and post-study physical examinations and laboratory investigations, ability to comprehend and willingness to sign statement of informed consent, and abstinence from tobacco during and three months prior to study. Female participants of childbearing age underwent a pregnancy test prior to each CsA dosing and, if positive, were excluded from the study. During the study period, reliable, non-hormonal methods of contraception had to be used.

Exclusion criteria included evidence of psychiatric disorder, history of or current abuse of drugs (including alcohol), use of any medication within two weeks prior to first administration of study medication, participation in another study with an experimental drug with administration within twelve weeks prior to the current study, major illness during the last three months, donation or loss of blood exceeding 500 mL during the eight weeks before the first administration of the study drug, positive test for Hepatitis B or C or HIV, positive urine drug screen, vaccination of any kind within four weeks of first dose or planning vaccination within three months of last dose, close family member receiving live vaccine during study or within three months post-study, and hypotension or hypertension during screening period.

History of any of the following diseases was also criterion for exclusion from the study: any type of malignancy, immunodeficiency, tendency toward recurrent infections, known untreated parasitic infection, allergy to any compound in the reference and test product, or to egg or soybean, any bronchiospastic diseases, epilepsy, porphyria, psoriasis, atopic dermatitis, hypercholesterolemia, gout, rheumatoid arthritis or kidney disease.

Care was taken to include both female and male participants both of Caucasian and non-Caucasian race. Written informed consent was obtained from all participants before study enrollment.

Sampling Period

Subjects were randomized into two treatment sequences: the test product followed by the reference product or vice versa. There was a washout period set to 14-21 days between the first and second treatment period. Participants reported to the clinic the night before treatment for laboratory testing, including blood samples, pregnancy test and urine drug screen, The subjects were instructed not to ingest any citrus fruits and/or apple or pineapple 72 h prior to start of infusion and, within 24 h, no alcohol or any caffeine-containing products were permitted. On the clinical day, the only food served before drug administration was a standardized breakfast. Through an indwelling IV cannula, the subjects received either 5 mg/kg CicloMulsion (test) or 5 mg/kg Sandimmune (reference), infused at a constant rate over 4 h with a syringe pump. The dose recommended for induction of immunosuppression with Sandimmune in clinical praxis is 3-6 mg/kg/day.

The same arm was used for administration during both treatment periods. All infusion equipment were compatible with both the reference and the test product. Through an IV cannula in the contra-lateral arm, a total of 22 blood samples for CsA analysis were obtained pre-dose and at 0.25, 0.5, 1, 1.5, 2, 2.5, 3, 3.5, 4, 4.5, 5, 6, 7, 8, 10, 14, 18, 24, 30, 36 and 48 h after start of infusion. All samples were collected in vials containing ethylenediaminetetraacetic acid (EDTA), labeled and stored at −70° C. until analysis. Whole blood CsA-concentration was assayed with liquid chromatography-mass spectrometry/mass spectrometry (LC-MS/MS). The method was validated according to current FDA guidelines (37). The lower limit of quantification (LLOQ) was 39.39 ng/mL and the mean CV was 3.5% for CsA. Complete sets of calibration standards and quality controls were included within each run.

Twenty-four hours after start of administration of study medication, subjects were allowed to leave the clinic, provided they returned for the subsequent collection of blood samples. Vital signs were monitored during the infusion and measured 2 h after completion of infusion and after the last blood sample was drawn. Meals and drinks during clinic days were standardized. Water was allowed ad libitum before and after infusion of study medication. Alcohol, caffeine, citrus fruit, apple and pineapple were not allowed until the last blood sample was drawn in each treatment period.

Tolerability Assessment

Each subject was carefully monitored for adverse events (AEs) during infusion, and was questioned on the study day for any symptoms of such events. AEs were graded as mild, moderate or severe according to the following definitions:

Mild: Causing no limitation of usual activities; the subject may experience slight discomfort.

Moderate: Causing some limitation of usual activities; the subject may experience annoying discomfort.

Severe: Causing inability to carry out usual activities; the subject may experience intolerable discomfort or pain.

The investigator deemed each AE in regard of causality to the administered medical product as "certain," "probable," "possible," "unlikely," "not related" or "not assessable." Every AE was coded with the Medical Dictionary for Regulatory Activities (MedDRA) and reported according to strict criteria.

The proportions of overall AEs and AEs per organ class were compared between CicloMulsion and Sandimmune by means of 95% confidence interval (CI) for the difference between paired proportions and p-values from McNemar's test.

Pharmacokinetics and Bioequivalence Assessment

Pharmacokinetic variables for CsA were calculated by use of non-compartmental methods using WINNONLIN® Professional Version 5.2 (Pharsight Corporation, Mountain View Calif., USA). Statistical analysis was made using SAS® Software Version 9.1 (SAS institute, Cary, N.C., USA). All values below LLOQ prior to first positive sample were substituted with zero. For the pharmacokinetic assessment, the terminal values below the LLOQ were ignored.

CicloMulsion was compared to Sandimmune with respect to a number of pharmacokinetic variables using analysis of variance (ANOVA) with sequence, subject within sequence, product and period effects on log-transformed data. The parameters compared were Area Under the CsA time-concentration Curves for time 0 to the time of last quantifiable concentration ($AUC_{0-t}$), time 0 h extrapolated to infinity ($AUC_{0-\infty}$), time 4 h extrapolated to infinity ($AUC_{4-\infty}$), time 0 to 4 h ($AUC_{0-4}$) and time 4 to the last quantifiable concentration ($AUC_{4-t}$), maximum blood CsA concentration ($C_{max}$), apparent terminal CsA half-life ($t_{1/2,z}$), blood CsA clearance (CL) and mean residence time (MRT). $C_{max}$, $AUC_{0-\infty}$, $AUC_{0-t}$ and $AUC_{4-\infty}$ were considered primary variables and the remaining secondary. Point estimates and 90% CI for the CicloMulsion/Sandimmune geometric mean ratios of all variables were calculated. The two products were considered bioequivalent if the 90% CI for the primary variables fell within the limits of 0.8 and 1.25.

Based on the FDA and EMA recommended bioequivalence range of 0.80 to 1.25 for Cmax, $AUC_{0-t}$ and $AUC_{0-\infty}$, an estimated within-subject coefficient of variation (CV) of 35%, and a "test/reference" mean ratio between 0.95 and 1.05, 52 subjects were needed to achieve a power of 80% at an alpha level of 0.05 to show bioequivalence (38).

Modifications in Study Design

The initial study design did not include any premedication, but, due to an unexpectedly high incidence of Serious Adverse Events (SAEs) to the reference product, the remainder of the study was performed with premedication. An amendment to the study protocol was written and approved by the ethical committees named above. For the sake of consistency, premedication was used prior to both CicloMulsion and Sandimmune even though the AEs triggering the instatement of premedication were observed following Sandimmune administration. Thirteen subjects completed both treatment periods without premedication. Eighteen subjects received the test product in the first treatment period without premedication, and received the reference product with premedication in second treatment period. The remainder (21 subjects) received premedication during both treatment periods, and thus with both the test and reference product.

The premedication consisted of one 50 mg capsule of diphenhydramine orally 1 h prior to commencement of infusion of test or reference drug, 10 mg dexamethasone by slow IV injection, and 50 mg ranitidine IV infusion over 5 minutes approximately 30 minutes prior to each dosing of study drug. The study was put on hold for the protocol amendments to be approved. This caused the washout period for the 18 subjects who received the test product in the first treatment period without premedication and the reference product with premedication in the second treatment period to be prolonged to more than six weeks. None of the premedications are known to change the pharmacokinetic properties of CsA or affect the bioanalytical assay.

Results

Sixty-five volunteers were enrolled in the study and randomized to a treatment sequence. Two subjects were withdrawn before first dosing due to illness, and eleven more withdrew before completion. Of these eleven, three were due to consent withdrawal, two due to investigator/sponsor decision (uncertainty of dose received due to problems with infusion), and six due to AEs. None of these subjects were included in the bioequivalence analysis. Fifty-two participants completed the study and were included in the pharmacokinetic evaluation. The demographics of the subjects completing the study are presented in Table 1.

TABLE 1

Demographics of subjects included in the pharmacokinetic study

|  | n = 52 |
|---|---|
| Gender |  |
| male/female | 33/19 |
| Age (years) |  |
| mean (range) | 24.4 (18-46) |
| Race |  |
| Caucasian/African/mixed heritage | 35/16/1 |
| Body Mass (kg) |  |
| mean (range) | 70.4 (60.0-99.8) |
| BMI (kg/m$^2$) |  |
| mean (range) | 23.3 (18.8-28.3) |

Sixty-three participants received at least one dose of study medication and were included in the overall tolerability assessment. Due to an unexpectedly high number of serious adverse reactions to Sandimmune, the study protocol was changed and premedication as described above introduced. The statistical analysis of incidence of AEs was performed solely including the thirteen participants who received both the test and reference drug without premedication.

Pharmacokinetics and Bioequivalence Assessment

Figure 4:
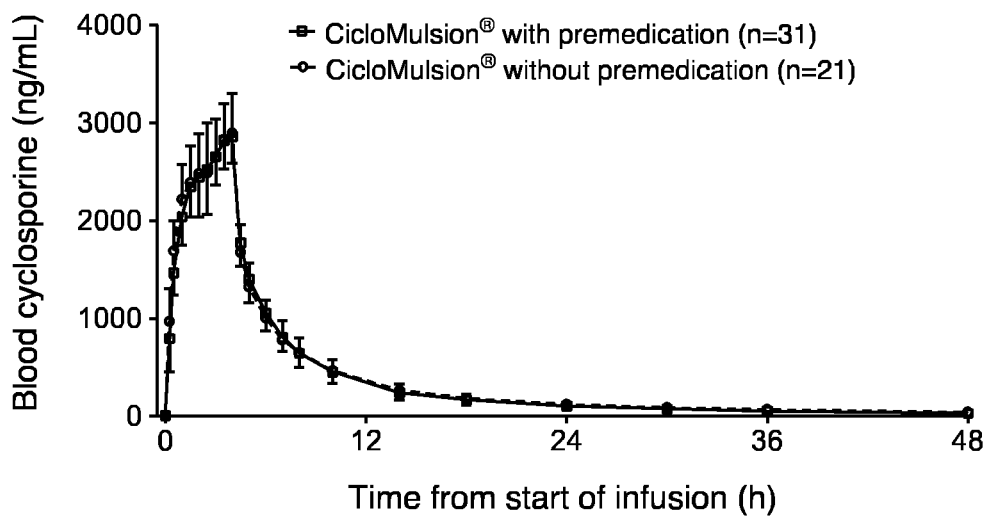
FIG. 4 shows mean blood Cyclosporine concentration with standard deviation in participants administered CicloMulsion (A) or Sandimmune (B) either with or without premedication consisting of 50 mg diphenhydramine orally, 10 mg dexamethasone intravenously and 50 mg ranitidine intravenously.
Figure 4:
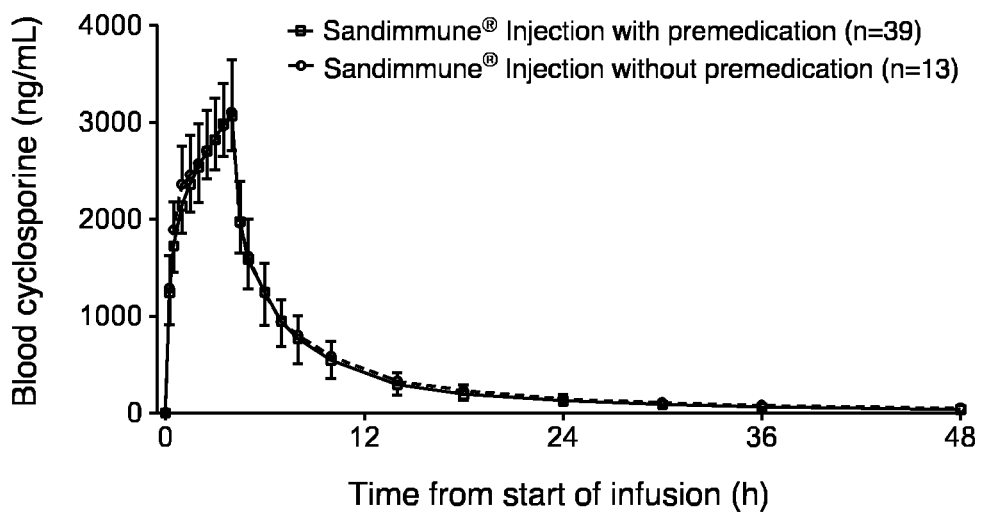

For each time point, arithmetic means with standard deviation were calculated for the whole blood CsA-concentrations for the test drug CicloMulsion and the reference drug Sandimmune. A graphical presentation of the CsA concentrations over time is provided in FIG. 1. In FIGS. 4A and B, time-concentration curves are presented separately for subjects receiving and not receiving concomitant premedication. The pharmacokinetic parameters are presented in Table 2.

TABLE 2

Pharmacokinetic parameters of Cyclosporine in subjects treated with CicloMulsion or Sandimmune as a single intravenous infusion over 4 h in the dose 5 mg/kg. Arithmetic means, standard deviation (SD) and coefficient of variation (CV).

| Parameter | CICLOMULSION ® (n = 52) | | | SANDIMMUNE ® Injection (n = 52) | | |
|---|---|---|---|---|---|---|
| (unit) | Mean | SD | CV % | Mean | SD | CV % |
| $C_{max}$ (ng/mL) | 2972 | 381 | 12.8 | 3134 | 386 | 12.3 |
| $AUC_{0-t}$ (h * ng/mL) | 19412 | 3202 | 16.5 | 21679 | 4165 | 19.2 |
| $AUC_{0-\infty}$ (h * ng/mL) | 20519 | 3488 | 17.0 | 22904 | 4466 | 19.5 |
| $AUC_{4-\infty}$ (h * ng/mL) | 11496 | 2569 | 22.3 | 13349 | 3626 | 27.2 |
| $AUC_{0-4}$ (h * ng/mL) | 9023 | 1232 | 13.7 | 9555 | 1148 | 12.0 |
| $AUC_{4-t}$ (h * ng/mL) | 10389 | 2240 | 21.6 | 12124 | 3256 | 26.9 |
| CL (mL/h) | 17446 | 2543 | 14.6 | 15746 | 2860 | 18.2 |
| MRT (h) | 8.8 | 3.2 | 36.1 | 9.1 | 5.8 | 63.5 |
| $t_{1/2,Z}$ (h) | 14.6 | 6.4 | 43.4 | 14.7 | 8.2 | 55.7 |
| AUC Extrapolation (%) | 5.3 | 2.5 | 46.6 | 5.2 | 4.0 | 76.7 |
| $T_{max}$ (h) | 3.7 | 0.4 | 11.4 | 3.7 | 0.4 | 10.1 |

The part of the $AUG_{0-\infty}$ that was extrapolated was approximately 5% for both of the study medications, indicating that a reliable estimate of the $AUC_{0-\infty}$ was obtained. No values below LLOQ were present between positive samples.

The statistical analysis of bioequivalence after dosing with CicloMulsion or Sandimmune is presented in Table 3. The point estimates of the CicloMulsion/Sandimmune geometric mean ratios (90% CI) of the primary variables $C_{max}$ and $AUC_{0-t}$ for CsA were 0.95 (0.92-0.97) and 0.90 (0.88-0.92), respectively, and $AUG_{0-\infty}$ and $AUC_{4-\infty}$ for CsA were 0.90 (0.88-0.92) and 0.87 (0.84-0.90), respectively. Thus, the 90% CI of all primary variables were within the range acceptable for bioequivalence of 0.80 to 1.25. The 90% CI for all secondary variables also met the criteria for bioequivalence.

TABLE 3

Assessment of bioequivalence of whole blood Cyclosporine exposure after dosing with a single dose of CicloMulsion (test) and Sandimmune Injection (reference). Geometric means of log-transformed data, standard deviation (SD), point estimates and 90% Confidence Interval (CI) of the CicloMulsion/Sandimmune Injection ratio and intrasubject coefficient of variation (CV).

| Parameter | Geometrical Mean and SD | | | | | | Intra- |
|---|---|---|---|---|---|---|---|
|  | CICLOMULSION ® | | SANDIMMUNE ® Injection | |  | 90% | subject CV |
| (unit) | Mean | SD | Mean | SD | Ratio | CI | (%) |
| $C_{max}$ (ng/mL) | 2949 | 371 | 3111 | 382 | 0.95 | (0.92-0.97) | 7.7 |
| $AUC_{0-t}$ (h * ng/mL) | 19157 | 3162 | 21315 | 3950 | 0.90 | (0.88-0.92) | 6.7 |
| $AUC_{0-\infty}$ (h * ng/mL) | 20235 | 3431 | 22507 | 4247 | 0.90 | (0.88-0.92) | 7.5 |
| $AUC_{4-\infty}$ (h * ng/mL) | 11216 | 2562 | 12906 | 3417 | 0.87 | (0.84-0.90) | 9.9 |

TABLE 3-continued

Assessment of bioequivalence of whole blood Cyclosporine
exposure after dosing with a single dose of CicloMulsion
(test) and Sandimmune Injection (reference).
Geometric means of log-transformed data, standard
deviation (SD), point estimates and 90% Confidence Interval
(CI) of the CicloMulsion/Sandimmune Injection ratio and
intrasubject coefficient of variation (CV).

| Parameter (unit) | Geometrical Mean and SD | | | | | | Intra-subject CV (%) |
|---|---|---|---|---|---|---|---|
| | CICLOMULSION ® | | SANDIMMUNE ® Injection | | | 90% | |
| | Mean | SD | Mean | SD | Ratio | CI | |
| $AUC_{0-4}$ (h * ng/mL) | 8943 | 1200 | 9490 | 1113 | 0.94 | (0.92-0.96) | 6.1 |
| $AUC_{4-t}$ (h * ng/mL) | 10150 | 2253 | 11732 | 3061 | 0.87 | (0.84-0.89) | 8.3 |
| CL (mL/h) | 17258 | 2608 | 15495 | 2837 | 1.11 | (1.09-1.14) | 7.5 |
| MRT (h) | 8.3 | 2.8 | 8.3 | 3.2 | 0.99 | (0.92-1.07) | 23.4 |
| $t_{1/2,z}$ (h) | 13.5 | 5.8 | 13.3 | 6.0 | 1.01 | (0.90-1.14) | 37.3 |

Tolerability

Out of 63 subjects, 55 reported one or more AEs. AEs graded as at least "possibly" related to the study medication were predominantly reported from the medDRA-coded organ classes of nervous system disorders and vascular disorders (Table 4). The nervous system disorders included headache, burning sensation, paresthesia, dizziness and sensory loss. The vascular disorders included events of hot flushes and orthostatic hypotension. When subjects received Sandimmune without premedication, 84% (16/19) experienced AEs assessed as at least possibly related to the study medication, compared to 64% (21/33) when they received CicloMulsion. With premedication, the figures were 76% (31/41) for Sandimmune and 67% (16/24) for CicloMulsion. Proportional analysis of AEs was performed for the subjects treated with both CicloMulsion and Sandimmune without premedication. There was a significantly higher proportion of overall AEs (p=0.003) and vascular disorders (p=0.03) when subjects were treated with Sandimmune. No other proportions were significantly different between the two formulations.

TABLE 4

Summary of all adverse events at least possibly related to study medication.
Number of patients (n) reporting adverse events and incidence in %. Presented with
and without premedication for CicloMulsion and Sandimmune Injection.

| | All Subjects | | Without premedication | | | | With premedication | | | |
|---|---|---|---|---|---|---|---|---|---|---|
| | | | SANDIMMUNE ® Injection | | CICLOMULSION ® | | SANDIMMUNE ® Injection | | CICLOMULSION ® | |
| | n | % | n | % | n | % | n | % | n | % |
| Number of subjects exposed | 63 | | 19 | | 33 | | 41 | | 24 | |
| Total number of subjects with adverse events | 54 | 86 | 16 | 84 | 21 | 64 | 31 | 76 | 16 | 67 |
| System organ class: | | | | | | | | | | |
| Nervous system disorders | 40 | 63 | 9 | 47 | 16 | 48 | 16 | 39 | 12 | 50 |
| Vascular disorders | 32 | 51 | 8 | 42 | 8 | 24 | 19 | 46 | 2 | 8 |
| Gastrointestinal disorders | 17 | 27 | 3 | 16 | 7 | 21 | 7 | 17 | 4 | 17 |
| Respiratory, thoracic and mediastinal disorders | 11 | 17 | — | — | 1 | 3 | 7 | 17 | 3 | 13 |
| Cardiac disorders | 6 | 10 | — | — | 1 | 3 | 3 | 7 | 3 | 13 |
| Immune system disorders | 6 | 10 | 4 | 21 | 1 | 3 | 1 | 2 | 1 | 4 |
| General disorders and administrative site conditions | 5 | 8 | — | — | 1 | 3 | 4 | 10 | 1 | 4 |

TABLE 4-continued

Summary of all adverse events at least possibly related to study medication.
Number of patients (n) reporting adverse events and incidence in %. Presented with
and without premedication for CicloMulsion and Sandimmune Injection.

|  | All Subjects | | Without premedication | | | | With premedication | | | |
|  |  |  | SANDIMMUNE ® Injection | | CICLOMULSION ® | | SANDIMMUNE ® Injection | | CICLOMULSION ® | |
|  | n | % | n | % | n | % | n | % | n | % |
| --- | --- | --- | --- | --- | --- | --- | --- | --- | --- | --- |
| Skin and subcutaneous tissue disorders | 4 | 6 | — | — | — | — | 3 | 7 | 1 | 4 |
| Renal and urinary disorders | 3 | 5 | — | — | — | — | 3 | 7 | 2 | 8 |
| Reproductive system and breast disorders | 3 | 5 | 1 | 5 | 1 | 3 | 1 | 2 | — | — |
| Musculoskeletal and connective tissue disorders | 2 | 3 | — | — | — | — | 2 | 5 | — | — |
| Eye disorders | 1 | 2 | 1 | 5 | — | — | — | — | — | — |
| Psychiatric disorders | 1 | 2 | 1 | 5 | — | — | — | — | — | — |

Two SAEs were recorded. The first affected a male, aged 21, who in the first treatment period was randomized to receive the reference medication, Sandimmune. Directly after start of infusion he experienced shortness of breath and a flushing sensation. Infusion was halted, treatment with 40% oxygen via Hudson mask was initiated, and he received promethazine 25 mg and hydrocortisone 200 mg IV. Due to continuing dyspnea, inhalation with nebulized salbutamol was commenced. Thirty-seven minutes after start of infusion the event was considered resolved and oxygen therapy was discontinued. The proceeding day, he left the clinic but reported feeling tired for another three days. The event was diagnosed as an anaphylactoid reaction.

The second of the two SAEs reported regarded a 42-year-old male who also received the reference drug Sandimmune in the first treatment period. Eleven minutes after infusion of the medication commenced he presented with coughing, facial flushing and dyspnea. Chest auscultation revealed wheezing sounds and the peripheral blood oxygen saturation ($SpO_2$) measured via pulse oxymeter was 95%. His condition quickly deteriorated, he became pale and sweaty, and a systolic/diastolic blood pressure of 75/42 mmHg was recorded. The infusion was stopped and therapy with 40% oxygen via Hudson mask and IV infusion with Ringer lactate commenced. Blood pressure was not rising and the $SpO_2$ dropped to 91% after a couple of minutes; he was treated with 0.5 mg adrenaline and 25 mg promethazine intramuscularly and 5 mg salbutamol as nebulized inhalation. An infusion of 200 mg hydrocortisone also commenced. Five minutes after the first medical intervention his blood pressure was normalized; within an hour all drug treatment could be discontinued. After 24 hours, treatment with IV fluids was halted and the subject could leave the clinic. He reported feeling fatigued for another five days but could carry out all normal activities. The event was diagnosed as an anaphylactic reaction. Both subjects were excluded from the remainder of the study.

Due to the events described above, as well as an allergic reaction considered moderate and possibly related to Sandimmune that also caused withdrawal of the subject, the study was put on hold and an amendment to the study protocol made with the addition of premedication as described above.

Three other subjects did not complete the study due to AEs. These were all moderate and possibly or probably related to the study medication. Out of these, two participants received the test product with premedication and one the reference product with premedication. No subjects receiving the test drug CicloMulsion without premedication were withdrawn due to AEs.

A summary of all AEs at least possibly related to the study medication is presented in Table 4. There were no clinically significant or consistent changes in laboratory values or ECG-findings due to CsA administration. Vital signs and clinical findings remained essentially unchanged during the study for all participants except for the two SAEs described above.

Discussion

After a single IV dose of 5 mg/kg, CicloMulsion and Sandimmune met the conventional criteria for bioequivalence. CicloMulsion was the better tolerated of the two CsA formulations.

Three patients had to be excluded from the study due to adverse reactions to Sandimmune, hence the study design was changed after a decision from local authorities. Due to this high incidence of SAEs in subjects receiving Sandimmune, premedication was introduced. The calculated pharmacokinetic parameters between subjects who did and did not receive premedication were similar, and bioequivalence could be established with a low intrasubject CV (for most variables under 10%) including premedicated and non-premedicated subjects. Thus, the changes in protocol and the introduction of premedication did not affect the pharmacokinetic profile of CsA.

In clinical practice, most CrEL-containing IV drugs (such as the anti-cancer agent Paclitaxel) are administered with premedication due to the known risk of hypersensitivity reactions to CrEL or, in the case of Sandimmune, is often given as a part of a combined regime with corticosteroids. It is feasible to assume that the actual incidence of adverse reactions to Sandimmune is obscured by the protective effect of the corticosteroids. A number of the reports of CrEL-reactions have been explained by improper dilution of the Sandimmune Injection concentrate. CrEL has a greater specific gravity than water and a high viscosity and, unless properly mixed, will not be equally partitioned in the infusion bottle. Concentrations of CrEL and CsA up to nine times higher than the intended dose have been reported during the first 10 minutes of infusion when mixed improperly (15, 27, 28). With a stable, ready-to-use preparation without the need for dilution, this would not be an issue.

When ALTHESIN was withdrawn in the late 1980s because of serious side effects due to CrEL, some authors argued that CrEL should not be used as a solvent for future drugs (39). Until now, CsA for IV administration has not been available with any other emulsifying excipient; this is surprising considering the extensive literature reporting serious or even fatal CrEL-related reactions (27, 40)

There are several previous studies comparing pharmacokinetics of orally administered CsA-formulations, but few for IV administration. In its oral form, CsA has frequently been found to have large variation in bioavailability between individuals (41-45) due to a number of factors, such as rate of gastric emptying, the rate of biliary, pancreatic and intestinal secretion, polymorphism in cytochrome P4503A enzymes, and different haplotypes of p-glycoprotein expressed in the gut wall mucosa. The intraindividual differences are usually explained by dietary factors and clinical condition (42-44, 46, 47).

There are examples of IV drugs in which the pharmacokinetic profiles have been significantly altered when a lipid emulsion was introduced as an emulsifier; known examples are Propofol and Diazepam (17, 48-50). Taking this into account, the estimated intraindividual coefficient of variation (CV) was estimated to 35% when designing the study. It turned out to be under 10% for all primary variables, supporting the view that most of the intrasubject variation in bioavailability is due to factors primarily relevant to the orally administered formulations of CsA. The interindividual CV % in this study was between 10% and 20% for Cmax, $AUC_{0-t}$ and $AUC_{0-\infty}$, consistent with previous reports for IV CsA (41, 51, 52). The ongoing debate about the switchability of brand and generic formulations of orally administered CsA for reasons of variability, should therefore not be extrapolated to IV formulations of the drug.

From the study, we conclude that CicloMulsion is bioequivalent to Sandimmune and that the ethanol- and CrE1-free, ready-to-use IV CsA formulation CicloMulsion is better tolerated

REFERENCES

1. Griveas I, Visvardis G, Papadopoulou D, Nakopolou L, Karanikas E, Gogos K et al. Effect of cyclosporine therapy with low doses of corticosteroids on idiopathic nephrotic syndrome. Artif Organs; 34(3):234-237.
2. Warren R B, Griffiths C E. Systemic therapies for psoriasis: methotrexate, retinoids, and cyclosporine. Clin Dermatol 2008; 26(5):438-447.
3. Fritsche L, Dragun D, Neumayer H H, Budde K. Impact of cyclosporine on the development of immunosuppressive therapy. Transplant Proc 2004; 36(2 Suppl):130S-134S.
4. Naganuma M, Fujii T, Watanabe M. The use of traditional and newer calcineurin inhibitors in inflammatory bowel disease. J Gastroenterol.
5. Hijnen D J, ten Berge 0, Timmer-de Mik L, Bruijnzeel-Koomen C A, de Bruin-Weller M S. Efficacy and safety of long-term treatment with cyclosporin A for atopic dermatitis. J Eur Acad Dermatol Venereol 2007; 21(1):85-89.
6. Kacmaz R O, Kempen J H, Newcomb C, Daniel E, Gangaputra S, Nussenblatt R B et al. Cyclosporine for ocular inflammatory diseases. Ophthalmology; 117(3):576-584.
7. Storb R, Antin J H, Cutler C. Should methotrexate plus calcineurin inhibitors be considered standard of care for prophylaxis of acute graft-versus-host disease? Biol Blood Marrow Transplant; 16(1 Suppl): S18-27.
8. Dorr R T. Pharmacology and toxicology of Cremophor EL diluent Ann Pharmacother 1994; 28(5 Suppl):S11-14.
9. Chapuis B, Helg C, Jeannet M, Zulian G, Huber P, Gumovski P. Anaphylactic reaction to intravenous cyclosporine. N Engl J Med 1985; 312(19):1259.
10. Kahan B D, Wideman C A, Flechner S, Vanburen C T. Anaphylactic Reaction to Intravenous Cyclosporin. Lancet 1984; 1(8367):52-52.
11. Leunissen K M L, Waterval P W G, Vanhooff J P. Anaphylactic Reaction to Intravenous Cyclosporin. Lancet 1985; 1(8429):636-636.
12. Friedman L S, Dienstag J L, Nelson P W, Russell P S, Cosimi A B. Anaphylactic Reaction and Cardiopulmonary Arrest Following Intravenous Cyclosporine. Am J Med 1985; 78(2):343-345.
13. Volcheck G W, Van Dellen R G. Anaphylaxis to intravenous cyclosporine and tolerance to oral cyclosporine: case report and review. Ann Allergy Asthma Immunol 1998; 80(2):159-163.
14. van Hooff J P, Bessems P, Beuman G H, Leunissen K M. Absence of allergic reaction to cyclosporin capsules in patient allergic to standard oral and intravenous solution of cyclosporin. Lancet 1987; 2(8573):1456.
15. Mackie F E, Umetsu D, Salvatierra 0, Sarwal M M. Pulmonary capillary leak syndrome with intravenous cyclosporin A in pediatric renal transplantation. Pediatr Transplant 2000; 4(1):35-38.
16. Howrie D L, Ptachcinski R J, Griffith B P, Hardesty R J, Rosenthal J T, Burckart G J et al. Anaphylactoid reactions associated with parenteral cyclosporine use: possible role of Cremophor EL. Drug Intell Clin Pharm 1985; 19(6): 425-427.
17. Baker M T, Naguib M. Propofol: the challenges of formulation. Anesthesiology 2005; 103(4):860-876.
18. Dye D, Watkins J. Suspected anaphylactic reaction to Cremophor EL. Br Med J 1980; 280(6228):1353.
19. Huttel M S, Schou Olesen A, Stoffersen E. Complement-mediated reactions to diazepam with Cremophor as solvent (Stesolid M R). Br J Anaesth 1980; 52(1):77-79.
20. Moneret-Vautrin D A, Laxenaire M C, Viry-Babel F. Anaphylaxis caused by anti-cremophor EL IgG STS antibodies in a case of reaction to althesin. Br J Anaesth 1983; 55(5):469-471.
21. Briggs L P, Clarke R S, Watkins J. An adverse reaction to the administration of disoprofol (Diprivan). Anaesthesia 1982; 37(11):1099-1101.
22. Thiel G, Hermle M, Brunner F P. Acutely impaired renal function during intravenous administration of cyclosporine A: a cremophore side-effect. Clin Nephrol 1986; 25 Suppl 1:S40-42.
23. Verani R. Cyclosporine nephrotoxicity in the Fischer rat. Clin Nephrol 1986; 25 Suppl 1:S9-13.
24. Windebank A J, Blexrud M D, de Groen P C. Potential neurotoxicity of the solvent vehicle for cyclosporine. J Pharmacol Exp Ther 1994; 268(2):1051-1056.
25. Sanchez H, Bigard X, Veksler V, Mettauer B, Lampert E, Lonsdorfer J et al. Immunosuppressive treatment affects cardiac and skeletal muscle mitochondria by the toxic effect of vehicle. J Mol Cell Cardiol 2000; 32(2):323-331.
26. Bowers V D, Locker S, Ames S, Jennings W, Corry R J. The hemodynamic effects of Cremophor-EL. Transplantation 1991; 51(4):847-850.

27. Theis J G, Liau-Chu M, Chan H S, Doyle J, Greenberg M L, Koren G. Anaphylactoid reactions in children receiving high-dose intravenous cyclosporine for reversal of tumor resistance: the causative role of improper dissolution of Cremophor EL. J Clin Oncol 1995; 13(10):2508-2516.
28. Liau-Chu M, Theis J G, Koren G. Mechanism of anaphylactoid reactions: improper preparation of high-dose intravenous cyclosporine leads to bolus infusion of Cremophor EL and cyclosporine. Ann Pharmacother 1997; 31(11):1287-1291.
29. Gotardo M A, Monteiro M. Migration of diethylhexyl phthalate from PVC bags into intravenous cyclosporine solutions. J Pharm Biomed Anal 2005; 38(4):709-713.
30. Venkataramanan R, Burckart G J, Ptachcinski R J, Blaha R, Logue L W, Bahnson A et al. Leaching of diethylhexyl phthalate from polyvinyl chloride bags into intravenous cyclosporine solution. Am J Hosp Pharm 1986; 43(11):2800-2802.
31. Trapani G, Altomare C, Liso G, Sanna E, Biggio G. Propofol in anesthesia. Mechanism of action, structure-activity relationships, and drug delivery. Curr Med Chem 2000; 7(2):249-271.
32. Mattila M A, Rossi M L, Ruoppi M K, Korhonen M, Loral H M, Kortelainen S. Reduction of venous sequelae of i.v. diazepam with a fat emulsion as solvent. Br J Anaesth 1981; 53(12):1265-1268.
33. Micha J P, Goldstein B H, Birk C L, Rettenmaier M A, Brown J V, 3rd. Abraxane in the treatment of ovarian cancer: the absence of hypersensitivity reactions. Gynecol Oncol 2006; 100(2):437-438.
34. Morgan M, Whitwam J G. Althesin. Anaesthesia 1985; 40(2):121-123.
35. Guidance for Industry: Statistical Approaches to Establishing Bioequivalence. United States Department of Health and Human Services, Food and Drug Administration (FDA) Rockville, Md., USA. 2001
36. Note for Guidance on the Investigation of Bioavailability and Bioequivalence. European Medicines Agency (EMA) CPMP/EWP/QWP/1401/98. London, Great Britain. 2001
37. Guidance for Industry: Bioanalytical Method Validation. United States Department of Health and Human Services, Food and Drug Administration (FDA) Rockville, Md., USA. 2001
38. Diletti E, Hauschke D, Steinijans V W. Sample size determination for bioequivalence assessment by means of confidence intervals. Int J Clin Pharmacol Ther Toxicol 1992; 30 Suppl 1:S51-58.
39. Kanto J H. Propofol, the newest induction agent of anesthesia. Int J Clin Pharmacol Ther Toxicol 1988; 26(1):41-57.
40. Kloover J S, den Bakker M A, Gelderblom H, van Meerbeeck J P. Fatal outcome of a hypersensitivity reaction to paclitaxel: a critical review of premedication regimens. Br J Cancer 2004; 90(2):304-305.
41. Gupta S K, Manfro R C, Tomlanovich S J, Gambertoglio J G, Garovoy M R, Benet L Z. Effect of food on the pharmacokinetics of cyclosporine in healthy subjects following oral and intravenous administration. J Clin Pharmacol 1990; 30(7):643-653.
42. Christians U, Klawitter J, Clavijo C F. Bioequivalence testing of immunosuppressants: concepts and misconceptions. Kidney Int Suppl (115):S1-7.
43. Christians U, First M R, Benet L Z. Recommendations for bioequivalence testing of cyclosporine generics revisited. Ther Drug Monit 2000; 22(3):330-345.
44. Kahan B D, Dunn J, Fitts C, Van Buren D, Wombolt D, Pollak R et al. Reduced inter- and intrasubject variability in cyclosporine pharmacokinetics in renal transplant recipients treated with a microemulsion formulation in conjunction with fasting, low-fat meals, or high-fat meals. Transplantation 1995; 59(4):505-511.
45. Kees F, Bucher M, Schweda F, Gschaidmeier H, Faerber L, Seifert R. Neoimmun versus Neoral: a bioequivalence study in healthy volunteers and influence of a fat-rich meal on the bioavailability of Neoimmun. Naunyn Schmiedebergs Arch Pharmacol 2007; 375(6):393-399.
46. Christians U, Schmitz V, Haschke M. Functional interactions between P-glycoprotein and CYP3A in drug metabolism. Expert Opin Drug Metab Toxicol 2005; 1(4):641-654.
47. Kovarik J M, Mueller E A, van Bree J B, Fluckiger S S, Lange H, Schmidt B et al. Cyclosporine pharmacokinetics and variability from a microemulsion formulation—a multicenter investigation in kidney transplant patients. Transplantation 1994; 58(6):658-663.
48. Dutta S, Matsumoto Y, Ebling W F. Propofol pharmacokinetics and pharmacodynamics assessed from a cremophor EL formulation. J Pharm Sci 1997; 86(8):967-969.
49. Fee J P, Dundee J W, Collier P S, McClean E. Bioavailability of intravenous diazepam. Lancet 1984; 2(8406):813.
50. Fee J P, Collier P S, Dundee J W. Bioavailability of three formulations of intravenous diazepam. Acta Anaesthesiol Scand 1986; 30(4):337-340.
51. Lee M, Min D I, Ku Y M, Flanigan M. Effect of grapefruit juice on pharmacokinetics of microemulsion cyclosporine in African American subjects compared with Caucasian subjects: does ethnic difference matter? J Clin Pharmacol 2001; 41(3):317-323.
52. Min D I, Lee M, Ku Y M, Flanigan M. Gender-dependent racial difference in disposition of cyclosporine among healthy African American and white volunteers. Clin Pharmacol Ther 2000; 68(5):478-486.

The invention claimed is:
1. A cyclosporine oil-in-water emulsion comprising
   i) 5 g/L cyclosporine,
   ii) 100 g/L soya bean oil,
   iii) 12 g/L egg lecithin,
   iv) 25 g/L water-free glycerol,
   v) 0.3 g/L sodium oleate,
   vi) 100 g/L medium chain triglyceride-oil selected from the group consisting of coconut oil, palm oil, and combinations thereof, and
   vii) water for injection,
wherein the emulsion is isoosmolar and has an osmolarity of from 280 to 305 mosm/l, and
wherein the composition does not contain polyethoxylated castor oil.
2. The cyclosporine emulsion according to claim 1 having an osmolarity of from about 295 to about 300 mosm/1.
3. The emulsion according to claim 1, wherein pH of the emulsion is from about 6 to about 8.8.
4. The cyclosporine emulsion of claim 1, further comprising: hydrochloric acid or sodium hydroxide for pH adjustment.

* * * * *